United States Patent
Heim et al.

[11] Patent Number: 6,074,387
[45] Date of Patent: Jun. 13, 2000

[54] ELECTROSURGICAL SYSTEM FOR REDUCING/REMOVING ESCHAR ACCUMULATIONS ON ELECTROSURGICAL INSTRUMENTS

[75] Inventors: Warren Paul Heim; Scott Allan Miller, III; James L. Brassell, all of Boulder, Colo.

[73] Assignee: Team Medical L.L.C., Boulder, Colo.

[21] Appl. No.: 08/951,982

[22] Filed: Oct. 15, 1997

[51] Int. Cl.[7] .................................................. A61B 17/39
[52] U.S. Cl. .............................................. 606/34; 128/898
[58] Field of Search ........................... 606/32–35, 37–42, 606/45–52; 604/21, 22, 114, 115; 128/898

[56] References Cited

U.S. PATENT DOCUMENTS

| | | |
|---|---|---|
| 3,900,823 | 8/1975 | Sokal et al. . |
| 3,919,656 | 11/1975 | Sokal et al. . |
| 4,087,878 | 5/1978 | Grieshaber et al. . |
| 4,184,197 | 1/1980 | Cuk et al. . |
| 4,186,437 | 1/1980 | Cuk . |
| 4,257,087 | 3/1981 | Cuk . |
| 4,274,133 | 6/1981 | Cuk et al. . |
| 4,307,720 | 12/1981 | Weber, Jr. ................................. 606/49 |
| 4,492,231 | 1/1985 | Auth . |
| 4,676,242 | 6/1987 | Doi . |
| 4,704,760 | 11/1987 | Grieshaber . |
| 4,752,983 | 6/1988 | Grieshaber . |
| 4,852,200 | 8/1989 | Phillips et al. . |
| 4,925,516 | 5/1990 | Phillips et al. . |
| 5,016,401 | 5/1991 | Mangus . |
| 5,078,078 | 1/1992 | Cuk . |
| 5,085,657 | 2/1992 | Ben-Simhon .............................. 606/42 |
| 5,088,997 | 2/1992 | Delahuerga et al. ..................... 606/42 |
| 5,167,659 | 12/1992 | Ohtomo et al. . |
| 5,197,963 | 3/1993 | Parins ......................................... 606/46 |
| 5,219,348 | 6/1993 | Buess et al. .............................. 606/49 |
| 5,313,943 | 5/1994 | Houser et al. . |
| 5,318,563 | 6/1994 | Malis et al. ............................... 606/38 |
| 5,322,503 | 6/1994 | Desai ......................................... 604/21 |
| 5,416,387 | 5/1995 | Cuk et al. . |
| 5,437,662 | 8/1995 | Nardella . |
| 5,442,534 | 8/1995 | Cuk et al. . |
| 5,442,539 | 8/1995 | Cuk et al. . |
| 5,472,443 | 12/1995 | Cordis et al. . |
| 5,539,630 | 7/1996 | Pietkiewicz et al. . |
| 5,540,681 | 7/1996 | Strul et al. . |
| 5,545,161 | 8/1996 | Imran . |
| 5,570,276 | 10/1996 | Cuk et al. . |
| 5,633,578 | 5/1997 | Eggers et al. . |

*Primary Examiner*—Michael Peffley
*Attorney, Agent, or Firm*—Holme Roberts & Owen LLP

[57] ABSTRACT

An electrosurgical system is disclosed that applies electrical energy to obtain a predetermined surgical effect, while also reducing eschar deposits on a working surface of an electrosurgical instrument, producing an eschar deposit which is easily removed from the working surface and/or facilitating removal of eschar deposits during a cleaning procedure. Such benefits may be realized by providing a negative bias on the working surface relative to a return path to source during electrosurgical procedures and/or during a cleaning procedure which may include contacting the working surface with an electrically conductive liquid.

48 Claims, 15 Drawing Sheets

ELECTROSURGICAL SYSTEM FOR REDUCING/REMOVING ESCHAR ACCUMULATIONS ON ELECTROSURGICAL INSTRUMENTS

FIELD OF THE INVENTION

The present invention relates to surgical methods and assemblies employing the application of electrical energy to tissue to achieve a predetermined surgical effect, and more particularly, to achieve such effect with reduced accumulation of bodily materials on the electrosurgical instrument. The invention further relates to methods and arrangements to facilitate removal of bodily materials that may accumulate on an electrosurgical instrument during surgical procedures.

BACKGROUND OF THE INVENTION

The potential uses and recognized advantages of employing electrical energy for surgical purposes are ever-increasing. In particular, for example, electrosurgical techniques are now being widely employed to provide highly-localized tissue cutting and coagulation capabilities in both open and laparoscopic applications, thereby yielding reduced tissue trauma and additional advantages relative to prior traditional surgical approaches.

Electrosurgical techniques entail the use of a hand-held instrument or pencil having one or more working surfaces that transfer radio frequency (RF) electrical energy to the tissue (e.g. via a stainless steel scalpel or blade), a source of radio frequency (RF) electrical energy (e.g. a dedicated electrosurgical generator), and a return path device, commonly in the form of a return electrode pad positioned under a patient or a smaller return electrode positionable in bodily contact at or immediately adjacent the surgical site. The return path device provides a return electrical path from the patient tissue to the energy source. More particularly, both the instrument and the return path device are interconnected via electrically conductive wire(s) to the source of the radio frequency electrical energy which serves as both the source and the sink for the electrical energy to produce a complete electrical circuit. When a hand-held instrument and return path pad are utilized, the electrosurgical technique is termed monopolar. When a hand-held instrument and smaller return path electrode (i.e. selectively positionable at or immediately adjacent the surgical site) are utilized the electrosurgical technique is termed bipolar.

The waveforms produced by the radio frequency electrical source may be designed to yield a predetermined electrosurgical effect, namely tissue cutting or coagulation. In this regard, prior to the present invention, tissue cutting/coagulation effects have been the sole parameters considered in the design of electrostirgical waveforms.

Despite the advantages associated with known electrosurgical techniques, one attendant implication has been that deposits build up on the surgical instrument working surfaces that convey electrical energy to the tissue. The deposits form from matter that is ejected from the tissue and contacts the working surfaces, and from tissue matter that directly contacts the working surfaces and stick thereto. The working surfaces typically heat up as the electrical energy is applied to them, which in turn causes the deposited materials to change their physical and chemical composition. The deposits are commonly referred to as eschar. As eschar builds up and becomes increasingly thick, it progressively detracts from the corresponding electrosurgical procedure (e.g. cutting). That is, for example, the eschar builds to such a thickness that a surgeon must interrupt the surgical procedure to clean the instrument's working surfaces. Cleaning commonly entails the use of abrasive pads that scrape the encrusted eschar from the working surfaces of the instrument. As the surgical procedure continues, the described cleaning procedure must be completed with increasing frequency. Such stoppages for cleaning interfere with the efficacy of the surgical procedure, cause delays and otherwise result in significant annoyance to medical practitioners.

In addition to the use of abrasive pads, other approaches to deal with eschar deposits have been restricted to treating electrosurgical blades with or making blades from materials intended to reduce eschar build-up. Such methods have included electropolishing stainless steel electrosurgical blades. Other methods have included covering the working surfaces with fluorinated hydrocarbon materials (see, e.g., U.S. Pat. No. 4,785,807), and coating niobium blades with a niobium oxide (see, e.g., U.S. Pat. No. 5,030,218). These approaches for eschar reduction still result in eschar deposits and require a focused effort on the part of medical practitioners to remove the eschar deposit from the working surfaces of the surgical instrument. Additionally, such cleaning frequently removes or otherwise degrades the special surface treatments of the working surfaces, which reduces their efficacy as the surgical procedure progresses.

SUMMARY OF THE INVENTION

Accordingly, a primary objective of the present invention is to provide an improved electrosurgical system for employing electrical energy to achieve a desired electrosurgical effect while reducing the amount of eschar deposited on the surgical instrument and the degree of adherence of such eschar.

Another objective of the present invention is to provide a method and apparatus for removing eschar accumulated on a surgical instrument, e.g. during an electrosurgical procedure.

A corresponding objective is to provide such improved systems, methods and devices in a cost effective and easy-to-use manner, including ready implementation and use with known electrosurgical generators.

In addressing one or more of these objectives, the present inventors have recognized that known RF electrosurgical waveforms yield average bias voltages that are at least equal to and in most cases greater than 0 volts. In connection with this recognition, and in one aspect of the present invention, a surgical system is provided which comprises the generation and application of a novel electrical energy waveform that provides for a negative average bias voltage on the working surface(s) of an electrosurgical instrument relative to a return path. For purposes hereof, "average bias voltage" and/or "mean bias voltage" are determined by integrating voltage output at the working surface(s) over a single, continuous period of operation of at least about three seconds, or over successive periods of operation totaling at least about three seconds, and dividing the result by the continuous or cumulative period(s) of operation. As will be further described, the amount of eschar deposit is significantly reduced utilizing the novel, negatively-biased waveform. Additionally, any deposit that does accumulate is more easily removed.

In another aspect of the present invention, the inventive system includes periodically applying an electrical signal to the working surface(s) of a surgical instrument and, at least partially contemporaneously, contacting the working surface with a medium to facilitate cleaning of deposits from the instrument. More particularly, the invention may comprise contacting the working surface(s) of an electrosurgical instrument with an electrically energized conductive liquid to enhance the removability of eschar accumulated on the working surfaces during electrosurgical procedures. Preferably, the working surfaces are held at a negative electrical potential relative to a conductive, return electrode that is also in contact with the conductive liquid to establish a complete circuit. As described later, the above-noted, advantageous cleaning effect results from the formation of gas bubbles on the working surface(s) which bubbles act to separate, or "lift", deposits from the working surfaces.

Benefits of the noted aspects of the present invention can be realized when the electrosurgical instrument working surfaces are made from traditional stainless steels commonly used for surgical instruments. Benefits can be enhanced by selecting working surface materials containing elements that have standard reduction potentials that are positive with respect to that of a standard hydrogen electrode. For example, use of one or more Group IB elements from the standard Periodic Chart of Elements, including copper, silver and gold, yields enhanced results.

As noted, the use of an electrosurgical waveform that provides for a negative average bias voltage at the working surfaces of an electrosurgical instrument relative to the return path serves to reduce eschar accumulation and lessen the degree of adhesion. In this regard, the inventors have found that the effect of reducing eschar build-up and/or producing a more easily removable eschar occurs even when a negative average bias voltage of only about 1 volt exists between the working surfaces of an electrosurgical scalpel blade relative to the return path device. Importantly, this negative bias of the working surfaces can be superimposed on known RF energy source (e.g. conventional electrosurgical generators) output waveforms employed to obtain predetermined tissue cutting and/or coagulative effects. As such, it should be understood that substantial portions of the electrical waveform applied to the working surfaces can be positive (i.e., relative to the return path device), so long as the average voltage bias is negative (i.e., relative to the return path device).

In one approach, negative biasing can be accomplished by simply shifting known RF waveforms "downward" via the series interconnection of a low voltage DC source (e.g. about 10 to 120 volts) with a conventional RF electrosurgical energy source. In another approach, a low frequency (LF) source (e.g. $\leq$ about 10 KHz.) output is combined with a conventional RF electrosurgical energy source output (e.g. $\geq$ about 100 KHz.) to yield a novel waveform having an average negative bias. In such approach, frequency-based shunting and/or blocking circuit components can be advantageously employed as means to electrically isolate each of the RF and LF sources. In yet another approach, an RF electrosurgical energy source can be advantageously employed to provide an RF output that is utilized by signal conversion means to generate an LF waveform that is combinable with the RF waveform to yield the desired negative biasing. Such signal conversion means may advantageously function to present a first resistance to current flow in one direction therethrough and a second resistance to current flow in the other direction therethrough, such first and second resistances being different. Preferably, a control means is included for selectively and variably establishing the difference between said first and second, directionally-dependant resistances.

As will be appreciated, other characteristics of the new electrical waveform (i.e. other than negative biasing), such as frequency and amplitude, can be provided as desired for cutting and/or coagulation as previously known in the art of electrosurgical generator design. Such frequencies can range from 100 kilohertz to 2 megahertz, and peak-to-peak voltages can range between about 10 and 15,000 volts. In this regard, the new waveforms may be approximately sinusoidal, dampened sinusoidal, or intermittent waveforms of approximately sinusoidal or dampened sinusoidal shapes, as previously known in the art. The various componentry for implementing negative-biasing features of the subject invention may be packaged separately and/or incorporated into and packaged with otherwise prior art electrosurgical generators.

When a conductive liquid is sprayed on to the working surfaces while the working surfaces are energized with the new electrosurgical waveform, the amount of eschar deposited may be further reduced. Such conductive liquid spray preferably comprises a biocompatible solution, including, for example, a normal saline solution. The spray mist may be applied using an external spray device separate from the surgical instrument or may be integrated into the surgical instrument. When the conductive spray is used in conjunction with an electrosurgical instrument having working surfaces made from a predetermined group of materials, such as metals comprising copper, eschar deposits do not appreciably accumulate and surgical procedures can proceed virtually without the need to remove eschar deposits.

As noted above, eschar removal from working surfaces of a surgical instrument is facilitated in accordance with the present invention by contacting the surfaces with an electrically conductive liquid and applying a negative voltage bias at the working surfaces relative to a return electrode also contacting the conductive liquid. In this regard, the inventive arrangement may define, in essence, an electrolytic cell, wherein the working surfaces act as a cathode and the return electrode acts as the anode. During operation, current flows via ion transfer from the return (or positive electrode) through the conductive solution to the electrosurgical instrument (or negative electrode), with electrons flowing from the electrosurgical instrument to the return electrode. The return electrode may be connected to a terminal of electrical energy source which predominantly has positive polarity, and the electrosurgical instrument may be connected to a terminal of the same electrical energy source which has a predominantly negative polarity. The magnitude of the polarities (i.e. voltages) can vary with time; however, higher voltages provide for faster cleaning. By way of example, eschar removal occurs expeditiously when a voltage source of at least about 10 volts is utilized. Currently, a voltage of between about 10 and 120 volts is preferable.

In operation, chemical reactions occur at the electrodes, and, by selecting suitable components for the electrolytic cell, it is possible to cause gas bubbles to form. By way of example, gas bubbles can be caused to form on the working surfaces (or negative electrode) due to electrolysis of substances in the electrically conductive liquid. In one arrangement, hydrogen gas bubbles can be made to evolve from the decomposition of water when the conductive solution is a saline solution, such as normal saline. Gas bubbles begin as minute accumulations of their constituent molecular entities and become larger as more molecules continue to aggregate. Gas bubbles form in various cracks and voids of whatever eschar has formed as well as on the eschar-free regions of the working surfaces. When bubbles start in regions that are constrained, such as small voids adjacent to or under eschar they are necessarily in a constrained volume and as the bubbles grow they produce a force on the adjacent eschar that causes the eschar to shift and, eventually, to lift off the working surface substrate on which the eschar deposit formed. Any residual adhesion of the eschar to the working surfaces comes from weak forces such as those caused by surface tension or van der Waals forces, and such weak forces are easily overcome by, for example, gentle wiping. Thus, deliberate formation of bubbles in the eschar, in this case using electrical energy, cause eschar to be loosened and to either be removed or become easily removable, from the working surfaces.

Preferably, in eschar removal/cleaning embodiments, the return electrode comprises one or more materials that do not readily corrode to discolor the conductive liquid and do not substantially change the resistance, either up or down, of the cell. In particular, electrode materials that produce corrosion products that bond to the electrode or that produce corrosion products that are substantially insoluble in the solution are desirable, including aluminum.

The electrical energy utilized for cleaning purposes may be derived from the output of a conventional RF energy source (e.g. electrosurgical generator) or may be provided separate from a electrosurgical generator. In one arrangement, the working surfaces of an electrosurgical instrument may be connected via a conductive element (e.g., insulated wire) to the negative terminal of a direct current (DC) power source, such as a battery pack, and an aluminum, return electrode can be connected to the positive terminal of the DC power source via a suitable conductive element (e.g., insulated wire). Alternatively, where an RF energy source is employed, a rectifying means may be used to provide a predominantly negative voltage at the electrosurgical instrument and predominantly positive voltage at the return electrode. The rectifying means may advantageously include one or more diodes, preferably with one or more transistor elements. Mechanical or electrical switching means may also be employed for establishing first and second circuit states corresponding with an electrosurgical procedure mode and a cleaning procedure. The electronic components for rectification, switching, etc. may be incorporated into the housings of one or more of the return electrode, the electrosurgical instrument, a cleaning assembly comprising the conductive fluid, or a separate device that interconnects one or more of these assemblies to each other or to the electrosurgical generator. In this manner, utilization of this aspect of the present invention also does not require modification of conventional electrosurgical generators in order to take advantage of cleaning benefits.

Preferably, the conductive liquid used for cleaning is one which is biologically acceptable, such as normal saline, although other biologically acceptable solutions such as ascorbic acid, sodium chloride and/or sodium bicarbonate solutions also produce the desired effect. The conductive liquid may be carried by an absorbent pad, such as a gauze pad, that is contacting a conductive metal foil that acts as a return electrode. In turn, the metal foil is electrically connected to the positive terminal of an electrical energy source using a conductive element, such as an insulated wire. The conductive element holds the metal foil at a positive voltage relative to the working surfaces of the instrument from which the eschar is being removed. In one embodiment, a clip may be employed so as to allow a moistened pad/conductive metal foil assembly to be removably attached to surgical drapes or other items in the surgical region so that a surgeon can conveniently wipe the working surfaces across the moistened pad to simultaneously loosen and wipe eschar deposits from the working surfaces in one motion.

Alternatively, the conductive liquid may be contained in a small vessel, wherein the liquid is electrically interconnected via separate conductive elements (e.g., via separate insulated wires) to the positive and negative terminals of a voltage source. In one approach, the vessel may be configured or an insert element provided (e.g. a woven, multilayered pad), to define a tortuous entry path that permits selective access of a surgical instrument into the vessel while substantially retaining the liquid therewithin. In another approach, one or more sealing members (e.g. resilient flaps or resealable material) may be utilized. In either case, the working surfaces of a surgical instrument may be selectively inserted into the vessel to contact the conductive liquid and, upon withdrawal, the insert element or sealing member may contact and facilitate removal of any eschar that may remain loosely adhered to the working surfaces. Advantageously, activation of the negative voltage delivery to the liquid may be automatically triggered using switches activated by the presence of the surgical instrument or its working surfaces or using an automatic sensor that determines when the working surfaces are in contact with the conductive liquid. More particularly, a sense signal, such as a low voltage alternating current signal of a specific frequency different than that used for obtaining an electrosurgical effect, may be transmitted to the surgical instrument and its working surfaces, and sensors monitoring the positive voltage conductive element can be used to sense the presence of such a signal, which would only be present when the working surfaces are electrically communicating with the positive electrode in the cleaning element, such as an aluminum electrode, via the working surfaces contacting the conductive liquid. Alternatively, similar switching or automatic sensing may be employed to provide for converting from an electrosurgical procedure mode to a cleaning mode when the RF electrical energy source is operating in the electrosurgical procedure mode. Switching may be accomplished using one or more mechanical switches comprising one or more movable elements that cause opening or closing of one or more electrical contacts, or switching may be accomplished using an electronic switch comprising one or more electronic components that enable or disable current flow paths (e.g. automatically).

It should be noted that electrosurgical procedures need not occur with use of above-noted average negative biasing aspects of the invention in order to realize benefits via use of the cleaning-related aspects of the present invention. That is, even when only known electrosurgical techniques are utilized, removal of eschar will still be facilitated when the working surfaces of an electrosurgical instrument are held at a substantially negative voltage and when contacted with a conductive liquid being held at a substantially positive relative voltage. However, cutting with the novel waveform noted above produces an eschar that is even more easily removed.

DETAILED DESCRIPTION

Figure 1:
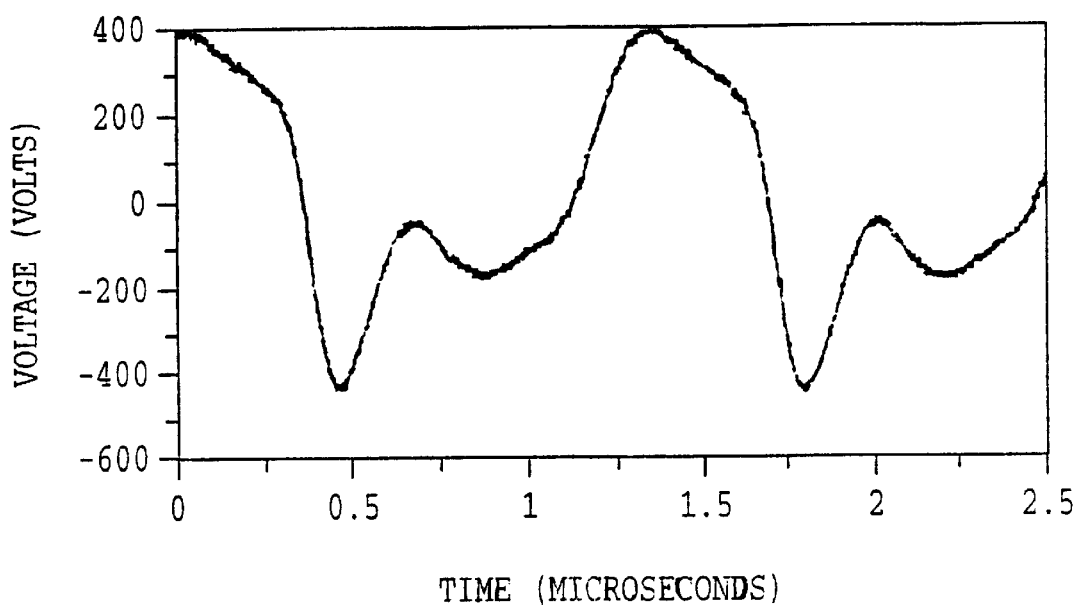
FIG. 1 illustrates an example of a prior art waveform (i.e. output by a prior art electrosurgical generator).

FIG. 1 illustrates an RF electrical waveform generated by a known electrosurgical generator for tissue cutting. As shown, the average voltage bias for the illustrated period of operation is greater than zero volts.

Figure 2:
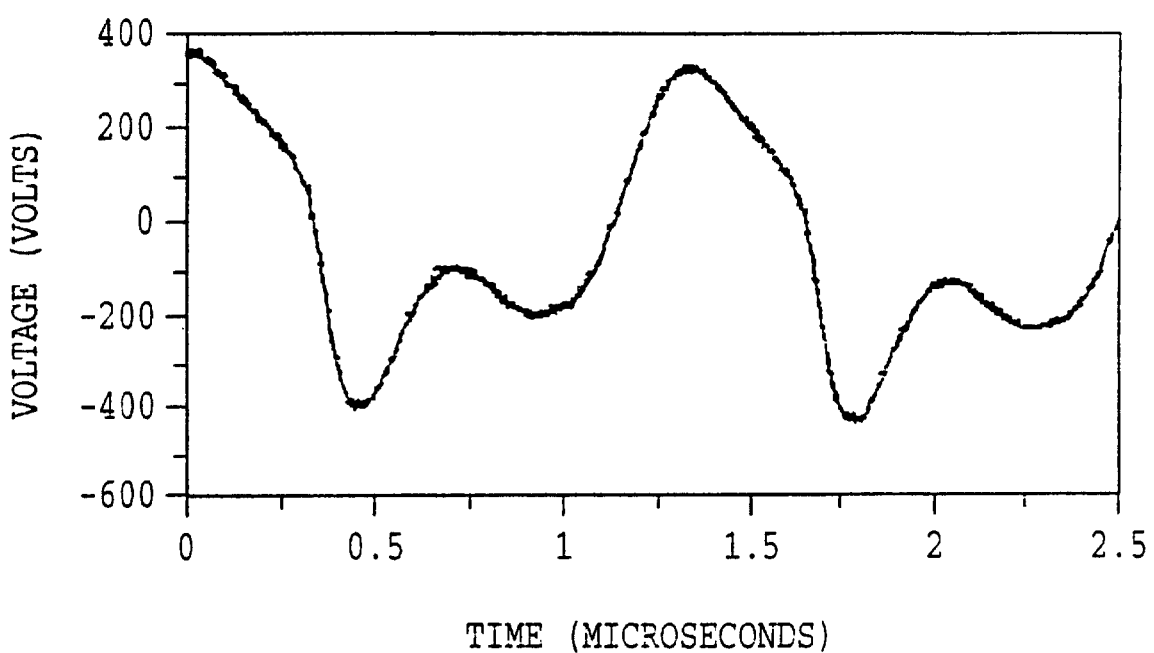
FIG. 2 illustrates one example of a novel electrosurgical waveform comprising the present invention, such waveform comprising a prior art waveform combined with a negative biasing waveform.

FIG. 2 illustrates an electrosurgical waveform that comprises one aspect of the present invention. In particular, FIG. 2 illustrates a novel waveform realized when an intentional negative bias is superimposed on a known waveform by displacing or shifting the known RF waveform of FIG. 1 with a negative DC voltage component. As will be appreciated, a negative bias can also be applied by changing the shape of known RF waveforms. In either case, the net result is that the average voltage bias is negative While one embodiment may employ both waveform shifting and waveform shaping means, either one by itself may be used to achieve the desired effects.

Figure 3:
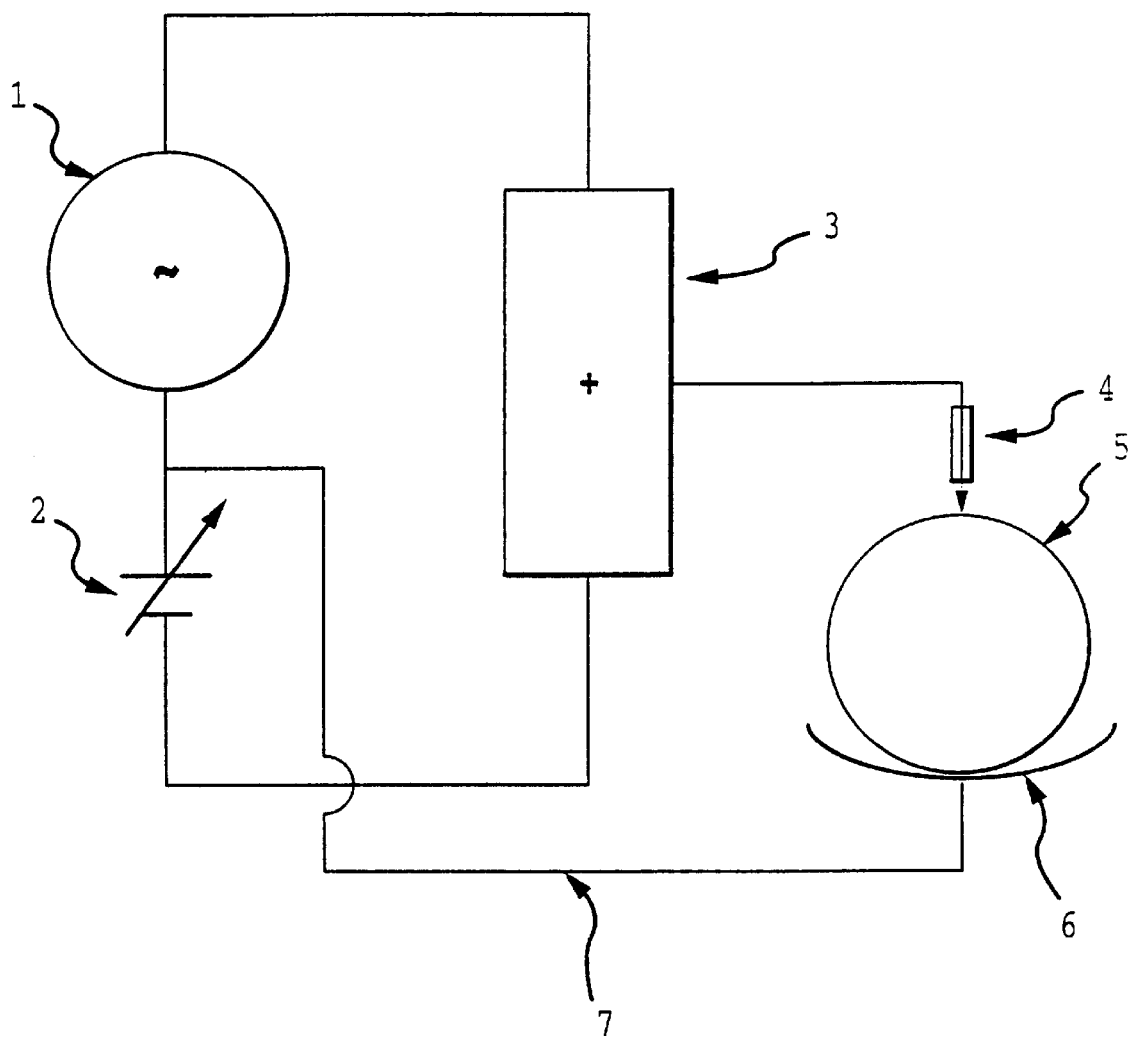
FIG. 3 is a block diagram illustrating one approach for producing a negatively biased waveform in a monopolar electrosurgery application, wherein a first radio frequency (RF) source and a secondary low frequency (LF) source produce two electrical waveforms that are combined.

For purposes of describing the first aspect of the present invention, FIGS. 3–5 show how a monopolar electrosurgical system may be configured to produce negatively biased electrosurgical waveforms. Without loss of generality, it is recognized that other embodiments besides those illustrated exist and can be derived from the principles illustrated in FIGS. 3 to 5 and the descriptions contained herein. In the various figures that follow components that have the same reference numbers provide the same or analogous functionality.

FIG. 3 is a block diagram of a negative biasing approach comprising a radio frequency (RF), AC electrical energy source 1 (e.g. $\geq 100$ kHz) and a low frequency (LF) electrical energy source 2 (e.g. $\leq 10$ kHz) that have their output electrical waveforms combined using suitable circuitry 3 to produce an output that goes to an electrosurgical instrument 4 from which electrical energy is applied to a patient 5. The electrical circuit is completed by having the patient 5 contact a return path electrode 6 that continues via electrical return path 7 to RF energy source 1. The RF source 1 typically operates at between about 250 kilohertz and 2 megahertz, and commonly has open circuit peak-to-peak voltages of approximately 2,000 to 15,000 volts and peak to peak voltages during use ranging from 600 volts to 15,000 volts. The RF electrical waveforms may be sinusoidal, dampened sinusoidal, or intermittent waveforms of approximately sinusoidal or dampened sinusoidal shapes. The means for producing such RF electrical waveform are known to those skilled in the art of electrosurgical generator design.

The LF source 2 is illustrated as a variable device and may produce a time varying LF electrical waveform. Without loss of generality, the LF source 2 can also be a direct current source that produces substantially direct current (e.g. from a battery or an isolated power supply). A source that adds a negative bias of at least about 1 volt to the output of the RF source 1 is desired. Further, for many applications it may be preferred that the negative-biasing source include a negative bias control device to provide more than one bias setting.

One setting would produce a negative average voltage bias of, for example, about 1.5 volts, when combined with the electrical waveform from the RF source 1. This setting would be used to reduce eschar accumulation and otherwise result in an eschar that is easily removed. Higher negative bias settings would be available to further reduce the amount of eschar formed, with such biases ranging up to about negative 60 volts. A negative average voltage bias of approximately 3 to 16 volts is currently most preferred. Practical limits on the amount of negative bias to be utilized may be determinable as appropriate to maintain the safety of health care personnel and the patient. In this regard, while the desired effects of reduced eschar deposits have been realized with voltages well in excess of 60 volts negative average bias, but such results are not practically different from those observed at much lower voltages.

The LF source 2 in FIG. 3 may also be employed for instrument cleaning (assembly not shown in FIG. 3). In this regard, various cleaning embodiments will be described in detail hereinbelow. Generally, for purposes of cleaning, a setting of the LF source 2 between approximately negative 10 to negative 120 volts is currently preferred to achieve rapid eschar removal. During operation for eschar removal, the RF source 1 does not need to continue to generate its electrosurgical waveform. However, eschar removal is not adversely affected if an RF electrosurgical waveform is utilized in conjunction with an LF waveform.

The RF source 1 and the LF source 2 can be controlled such that they apply power when switched using hand-triggered controls on the electrosurgical instrument 4 and/or controls on a separate device such as a foot switch. Such control means are known to those familiar with the art. Furthermore, and as subsequently described, controls can be incorporated such that whenever the RF source 1 is activated the LF source 2 is activated at the same time, and such that the LF source 2 can be operated without the RF source 1 being active. Such controls allow surgical procedures to always use the combined waveforms and allow eschar cleaning procedures to use only the waveform from the LF source 2. Additional control means will allow the LF source 2 to produce electrical waveforms, such as those using a low voltage, when activated in conjunction with the RF source 1 and another waveform, such as those using a high voltage, when operating without the RF source 1. Such operation could be used during cleaning procedures for eschar removal.

Figure 4A:
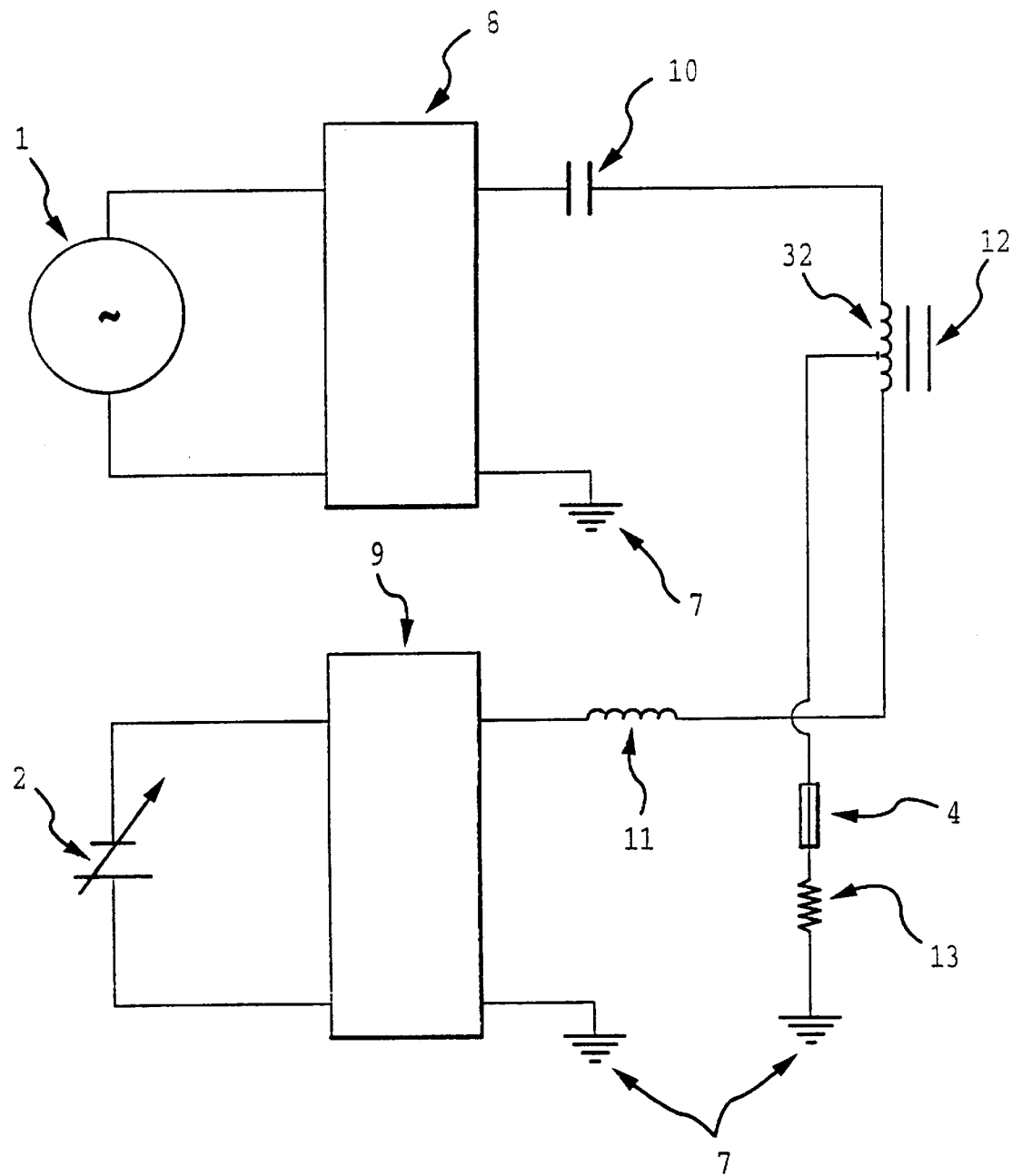
FIGS. 4A–4C illustrate electrical circuit topologies of various embodiments corresponding with the block diagram of FIG. 3.

FIG. 4A illustrates one circuit embodiment to combine the outputs from the RF source 1 and the LF source 1. A low frequency shunting filter 8 (e.g., $\leq 10$ kHz.) and a high frequency shunting filter 9 (e.g., $\geq 100$ kHz.) are provided in the circuit. The circuit also includes a low frequency blocking capacitor 10 (e.g., $\leq 10$ kHz.) and a high frequency blocking inductor 11 (e.g., $\geq 100$ kHz). The shunting filters 8, 9 and blocking components 10, 11, are utilized as isolation means to protect the RF source 1 from the effects of the LF source 2, and to protect the LF source 2 from the effects of the RF source 1. More than one of each type of shunting/blocking element can be used to improve performance or reduce cost. The output to surgical instrument 4 comes from a tap 32 on an inductive coupler 12. The system's "load" is represented by a patient load 13.

Figure 4B:
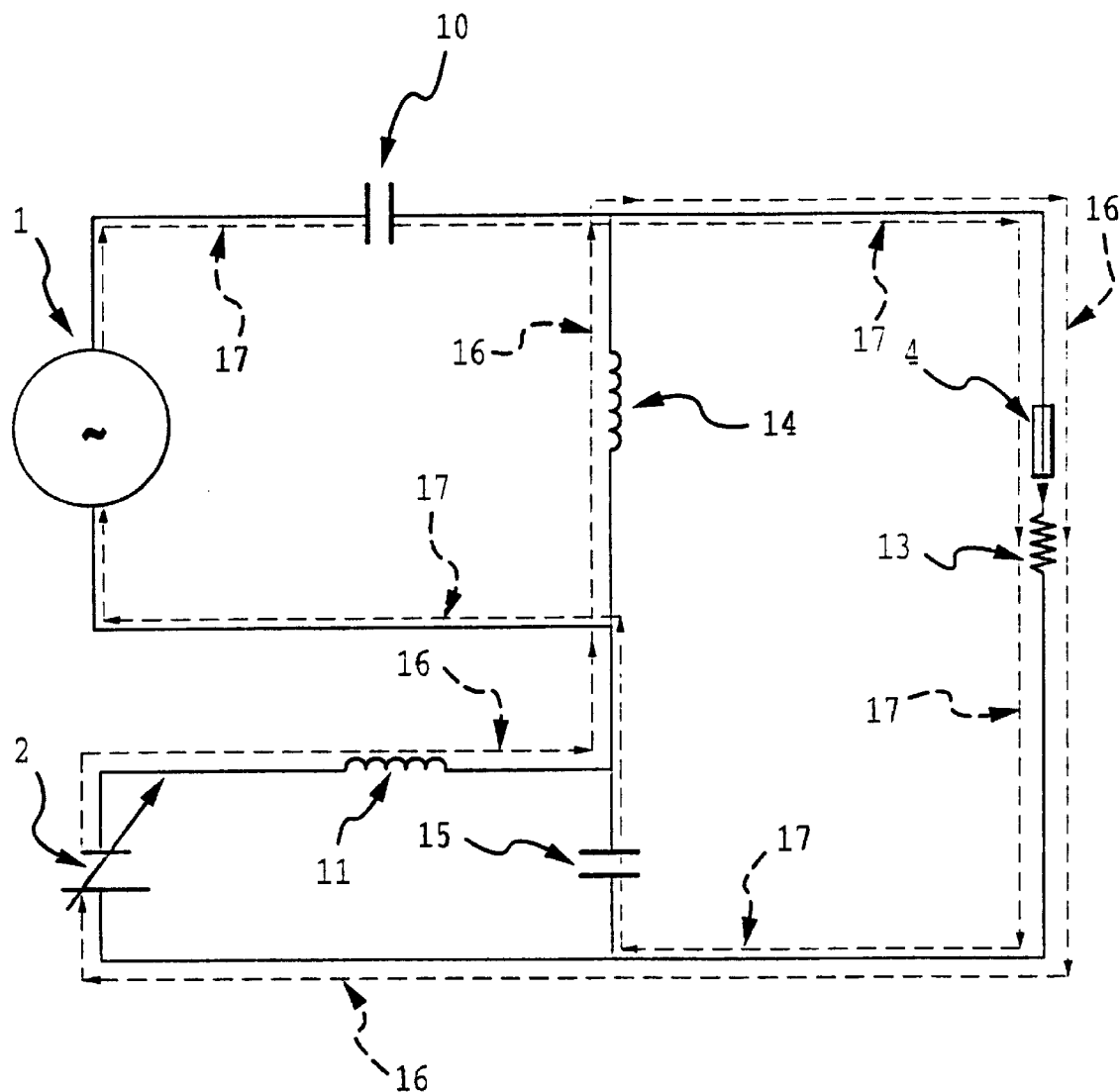

FIG. 4B illustrates another circuit embodiment for combining the outputs from RF source 1 and LF source 2. Low frequency shunting inductor 14 and high frequency shunting capacitor 15 are included. The low frequency signal path 16 (i.e. from/to LF source 2) and the high frequency signal path 17 (i.e. from to RF source 1) are shown. Both paths pass through the electrosurgical instrument 4 to the patient (represented as load 13), thus adding, or combining, the electrical energy waveforms from the RF source 1 and the LF source 2. The low frequency blocking capacitor 10 protects the RF source 1 from the LF source 2. The high frequency blocking inductor 11 protects the LF source 2 from the RF source 1. The blocking capacitor 10 may be one or more of the output blocking capacitors normally found in known RF electrosurgical generator output circuits.

Figure 4C:
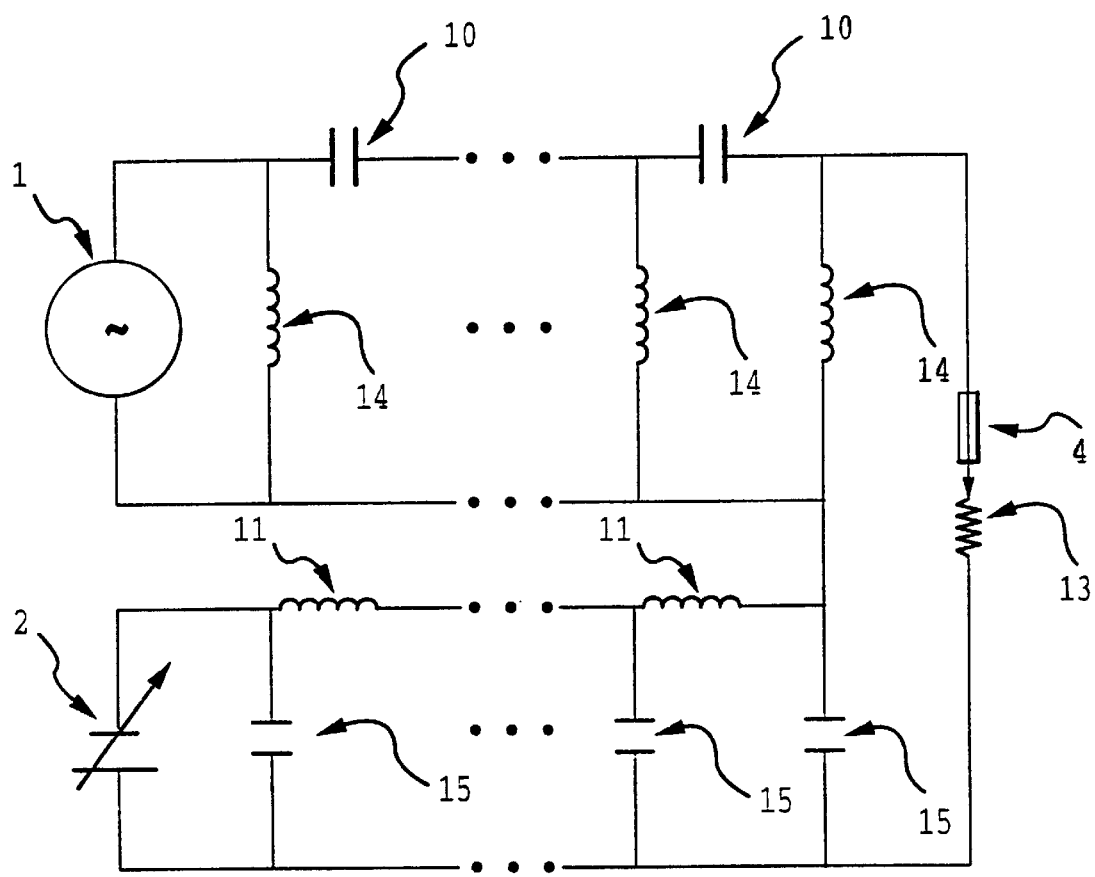

FIG. 4C illustrates how multiple shunting components 14, 15 and blocking components 10, 11 can be cascaded to make a more effective circuit. The advantages include more effective isolation of the RF source 1 and LF source 2 from each other. Additionally, the capacitance of the cascaded capacitors 10 can be established to advantageously reduce neuromuscular stimulation. More particularly, if a blocking capacitor 10 adjacent to electrosurgical instrument 4 is too large, then the making and breaking of contact between the instrument 4 and the patient load 13, as routinely occurs during surgical procedures, leads to substantial charge being stored in the blocking capacitor 10. Such substantial charge may cause neuromuscular stimulation. This effect can be reduced or otherwise substantially avoided by using a plurality of blocking capacitors 10 in a series arrangement, each of such capacitors having a suitably small value.

Figure 5A:
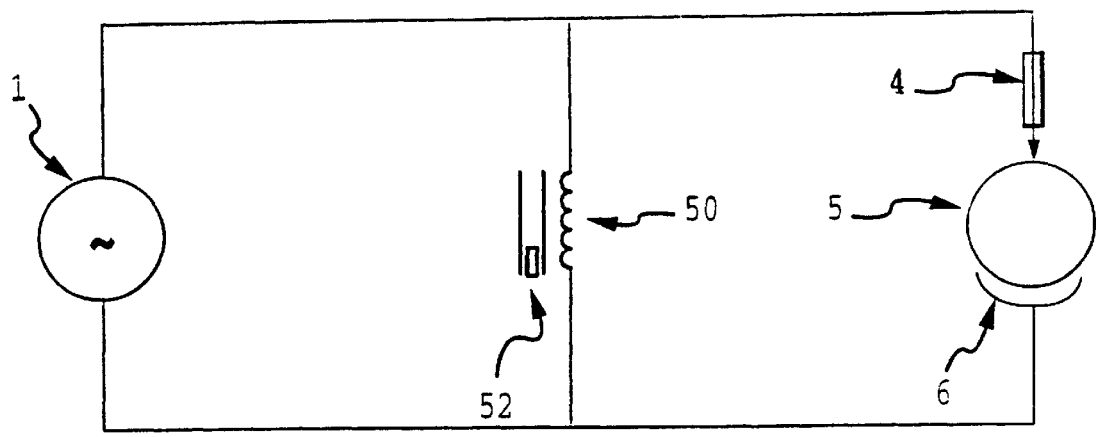
FIGS. 5A–5E illustrate various embodiments of an alternative approach for producing a negatively biased waveform in a monopolar electrosurgery application, wherein an RF source is employed to produce an RF waveform which is conditioned to provide an LF waveform for negative biasing.

FIGS. 5A–5E illustrate various embodiments that utilize an RF signal waveform to generate an LF signal waveform that is combined with the RF signal to yield negative biasing (i.e. a negative average voltage bias). In particular, FIG. 5A illustrates an embodiment in which the core of an inductor 50 is provided with a permanent magnet 52 to yield a negatively biased LF signal component that combines with an RF signal component from RF source 1 and is provided to electrosurgical instrument 4. More particularly, the core of inductor 50 may comprise a saturable, powdered iron ring having a portion thereof replaced with a permanent magnet. The polarity of such magnet provides for a differential saturation depending upon the signal direction therethrough. The reversing magnetic fields induced by the alternating current nature of the electrical current produced by RF source 1 are opposed by the inductance of inductor 50. However, the magnetic bias produced by permanent magnet 52 causes such inductor 50-induced opposition to preferentially favor current flowing in one direction and preferentially oppose current flowing in the opposite direction. The net result is a greater voltage drop in one direction than the other, which in the illustrated arrangement results in a negative biased voltage being applied to the instrument 4.

Figure 5B:
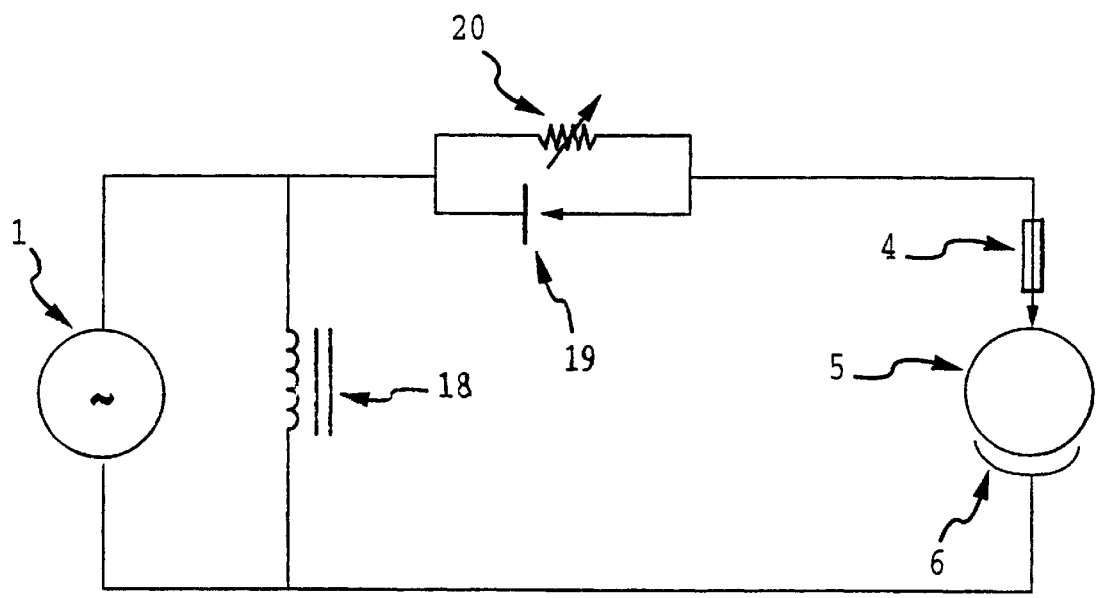

FIG. 5B illustrates another embodiment in which the source of the LF electrical energy waveform is derived from the RF source 1. A low frequency pass element 18 provides a path for the LF signal which comes from a rectifier 19. The voltage of the waveform is adjusted using voltage adjustment element 20. Voltage adjustment element 20 may be one or more electronic elements such as resistors or capacitors or an assembly of one or more such electronic elements. Rectifier 19, which may be one or more diodes and associated filter elements such as capacitors, defines a low resistance path for current flowing in one direction and a high resistance path for current flowing in the opposite direction. Voltage adjustment element 20 provides an equal resistance to current flowing in both directions. The result is a preferential current flow for a predetermined direction, which in the illustrated arrangement results in a negative biased voltage being applied to electrosurgical instrument 4.

Figure 5C:
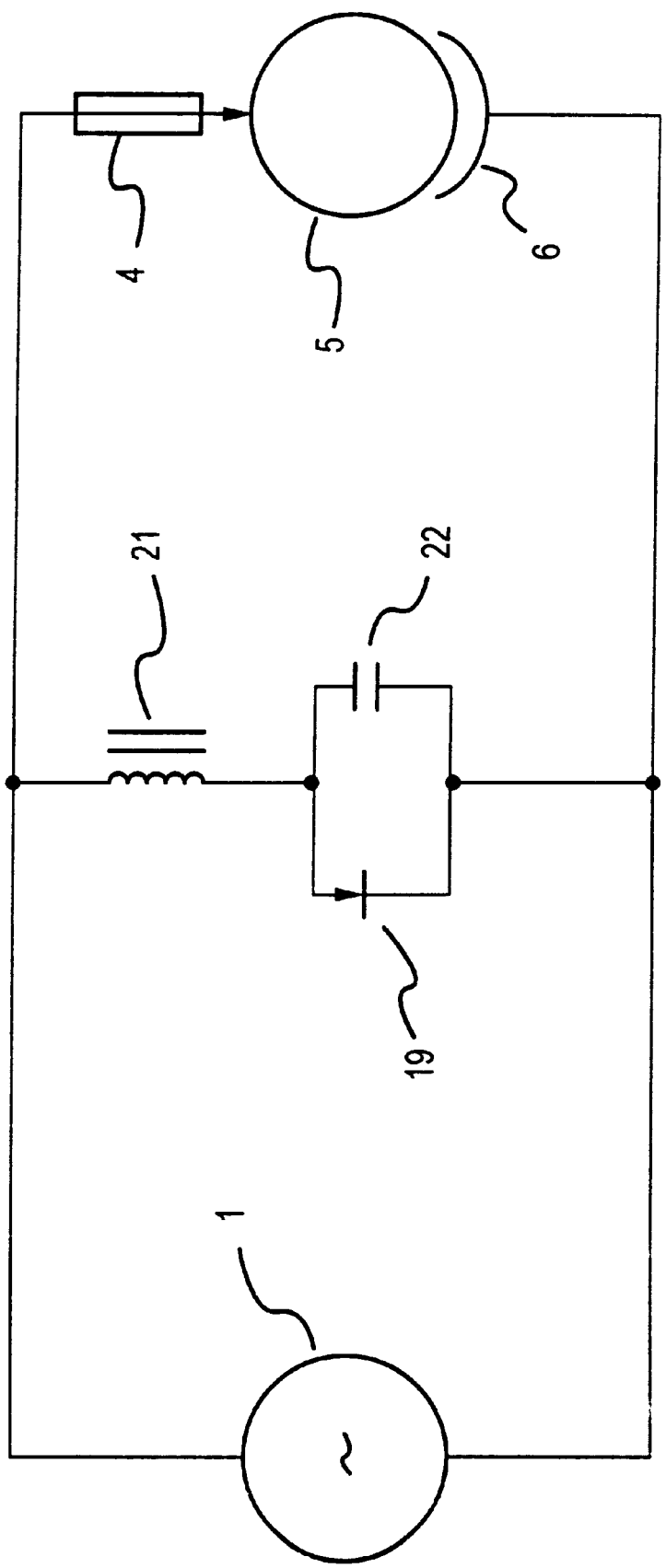
Figure 5D:
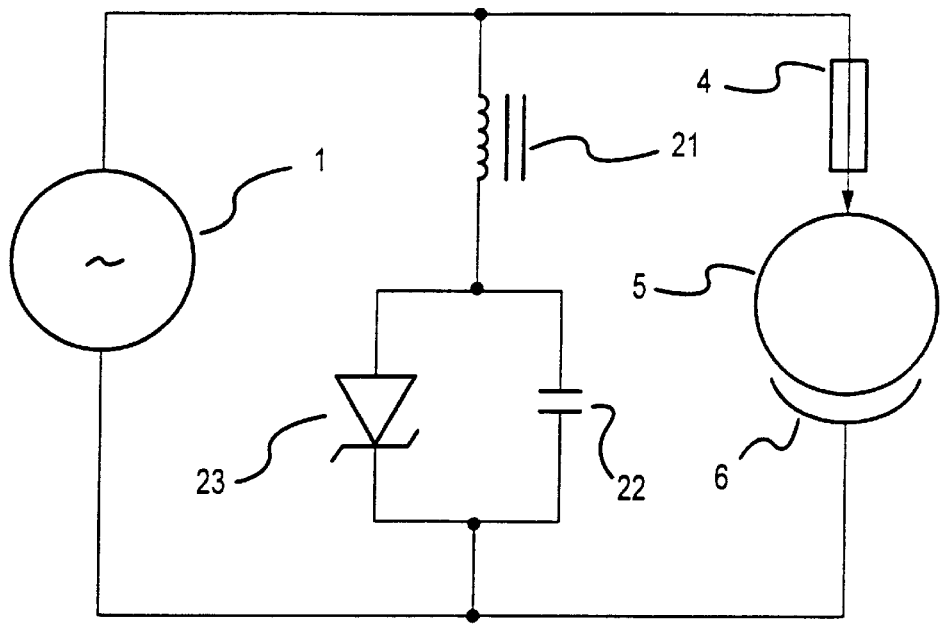

FIG. 5C illustrates yet another embodiment in which the source of the LF electrical energy waveform is derived from the RF source 1. A high frequency block 21, high frequency shunt 22, and rectifier 19 form a voltage divider that produces a low voltage biased DC. The bias voltage is dependent upon the impedance values of the RF block 21 and RF shunt 22. For example, where the impedances of RF block 21 and RF shunt 22 are selected using known design principles the voltage drops across these elements can be used to produce a wide range of biased voltages. Typical values may be about 100 microhenries for the RF block 21 and 10 picofarads for the RF shunt 22, with the resulting bias depending upon the frequency of the RF source 1, but which can be determined using methods known to those skilled in the art. FIG. 5D illustrates a similar arrangement.

Figure 5E:
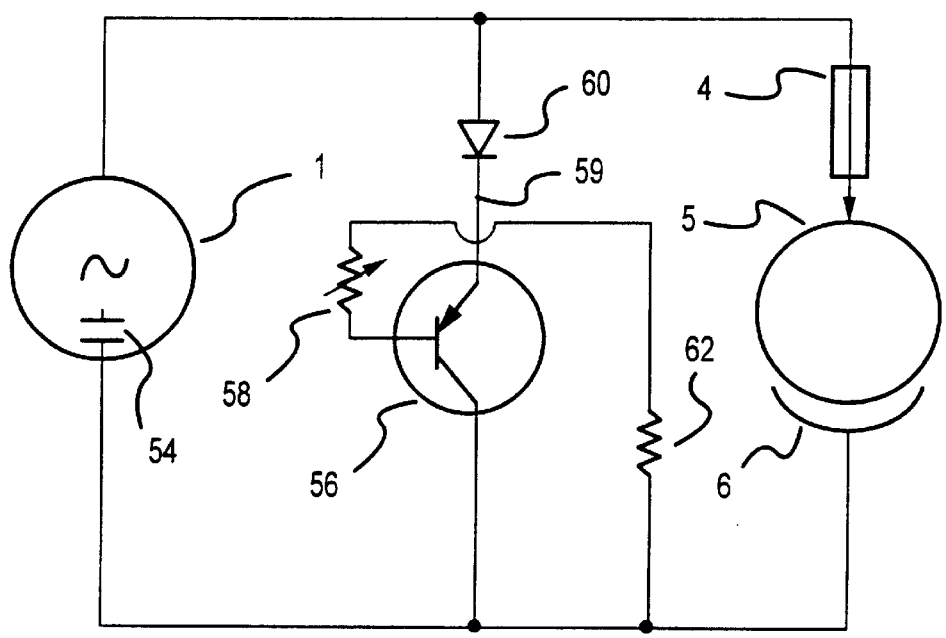

FIG. 5E illustrates a further embodiment in which the LF electrical energy waveform is derived from a radio frequency source 1, which in this case may again be a standard electrosurgical generator having an internal blocking capacitor 54. The circuit further utilizes a transistor 56, a resistive control element 58, a diode 60 and a resistor 62. When the electrosurgical generator 1 is operating, the diode 60 serves to cause a positive bias to occur in the circuit line 59 between diode 60 and transistor 56. The level of such bias is determined by the resistance values of resistive control element 58 and resistor 62. Such bias can be advantageously, selectively established since resistive element 58 is controllable.

In relation to another aspect of the present invention, FIGS. 6A–6F illustrate various embodiments for cleaning or removing eschar that may accumulate on the working surfaces of an electrosurgical instrument 4. For purposes of description, a monopolar configuration with a conventional electrosurgical generator 1 and a typical electrosurgical instrument 4 is utilized, wherein the instrument 4 is illustrated as being in electrical contact with either a patient 5 or a cleaning assembly 64 (i.e. illustrated via phantom lines), as will be selectively determined by user manipulation of instrument 4. It should be recognized by those skilled in the art that the embodiments of FIGS. 6A–6F illustrate principles that can be applied to a wide range of applications and that such principles are not limited to monopolar applications.

Figure 6A:
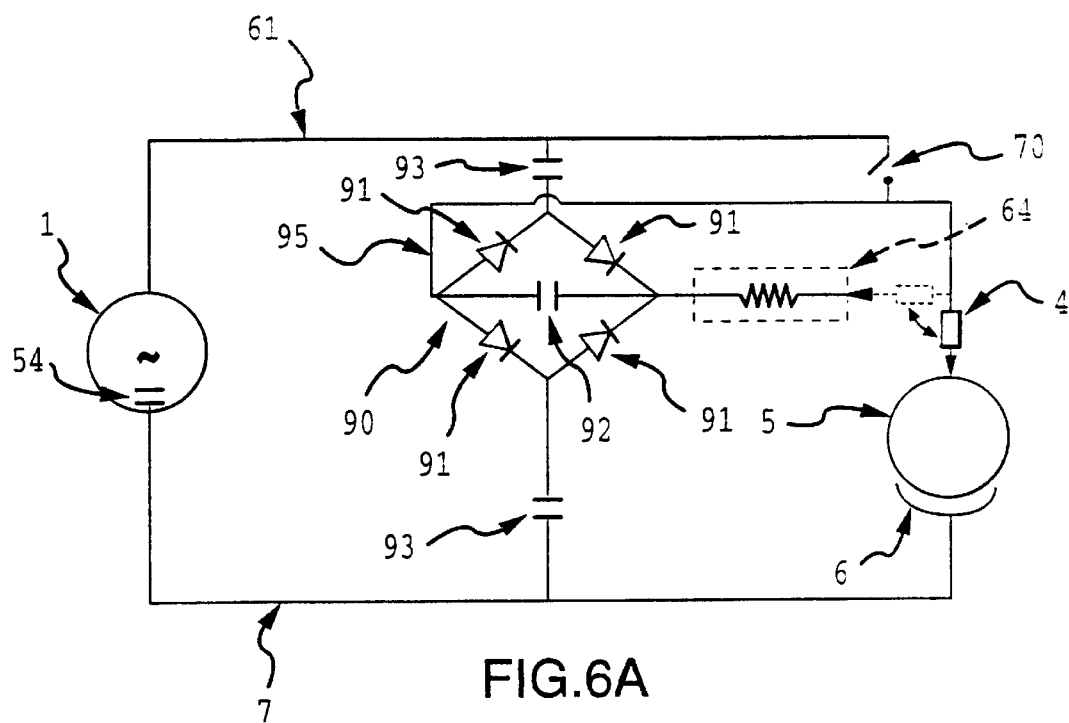
FIGS. 6A–6F illustrate various embodiments for selectively utilizing an RF electrosurgical source to clean an electrosurgical instrument.

FIG. 6A specifically illustrates an embodiment in which a conventional electrosurgical generator 1 provides an electrosurgical waveform to electrosurgical instrument 4 for electrosurgical procedures when mechanical switch 70 is closed, and which provides electrical energy for cleaning of the electrosurgical instrument 4 when mechanical switch 70 is selectively opened (e.g. by a user). In this embodiment, the electrosurgical generator 1 includes a blocking capacitor 54 internal thereto. The return electrode line 7, interconnected to return electrode 6, as well as the power line 61, interconnectable to electrosurgical instrument 4, may both terminate at simple connectors or jacks (not shown), which in turn may be selectively interconnected to electrosurgical generator 1. As will be appreciated, such an arrangement accommodates the ready use of conventional electrosurgical generators.

Voltage setting capacitors 93 and the rectifier bridge 90, comprising diodes 91, collectively serve to set a voltage delivered to electrosurgical instrument 4 via cleaning power line 95, as well as to rectify such voltage for cleaning purposes. A filter capacitor 92 smooths the output voltage to cleaning power line 95. Using the voltage setting capacitors 93 (e.g. instead of a resistor), avoids heat dissipation management considerations. The filter capacitor 92 produces voltages that consistently stay above zero volts, thereby facilitating operation of cleaning assembly 64 when electrosurgical instrument 4 is selectively brought into contact with cleaning assembly 64. As previously noted, mechanical switch 70 is closed during normal surgical procedures. Switch 70 is opened when the user wishes to clean electrosurgical instrument 4. Mechanical switch 70 may be conveniently incorporated as a separate button on the handle of the electrosurgical instrument 4, such as the handle of an electrosurgical pencil, or alternatively mechanical switch 70 could be incorporated into the cleaning assembly 64.

Figure 6C:
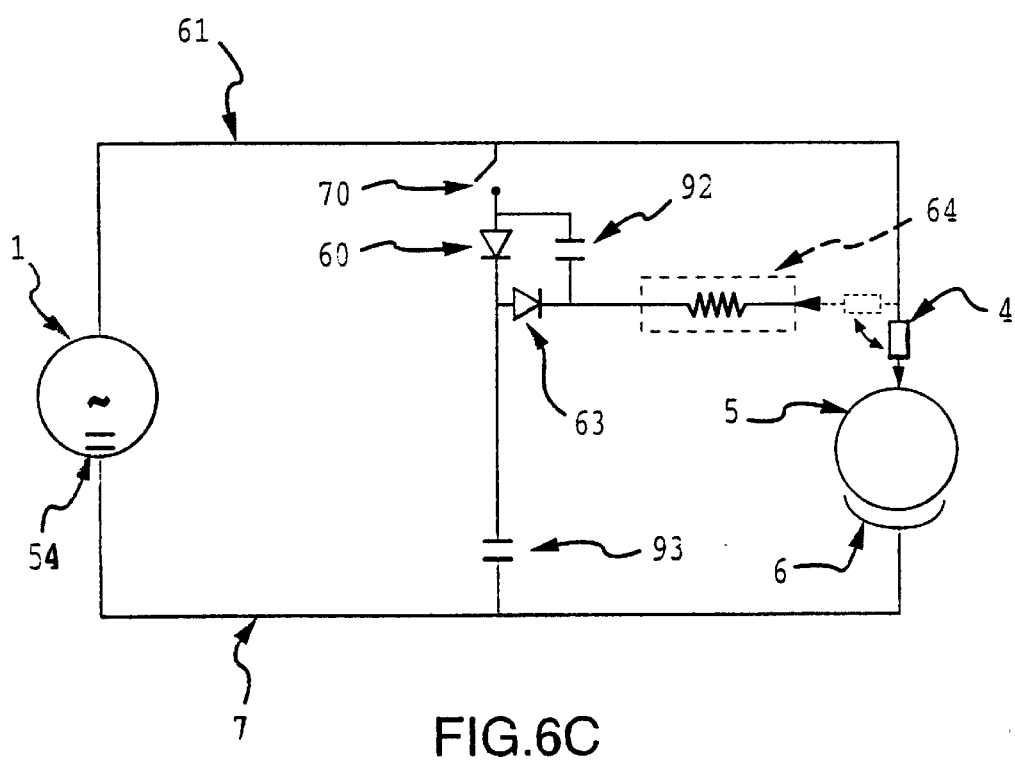
Figure 6B:
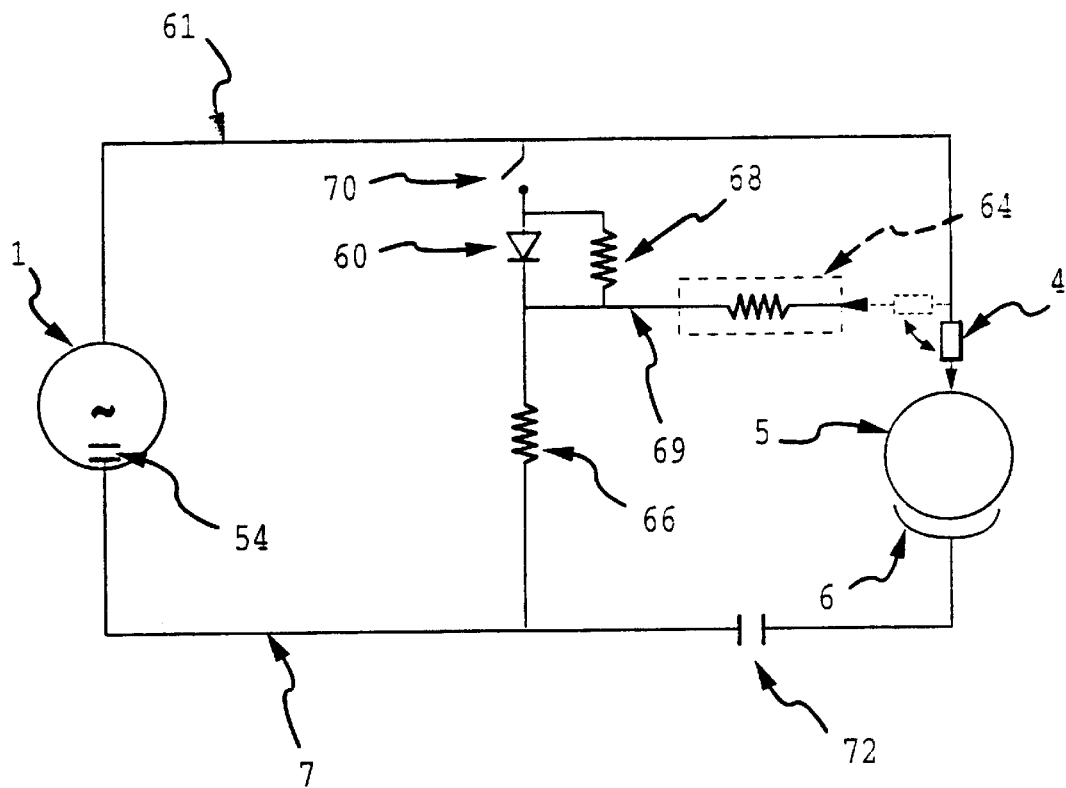

FIG. 6B illustrates an arrangement having an RF source 1, such as a standard, electrosurgical generator, which internally includes a blocking capacitor 54. In this arrangement, blocking capacitor 54 is utilized to produce a suitably biased current for cleaning electrosurgical instrument 4 utilizing a cleaning assembly 64. For purposes of illustration, the blocking capacitor 54 is shown connected to the line 7 between return electrode 6 and RF source 1. Alternatively, the blocking capacitor 54 could be connected to the line 61 between source 1 and electrosurgical instrument 4. As will be appreciated, power supply line 61 and return line 7 may each terminate at suitable connectors or jacks (not shown) for selective and ready interconnection with a standard electrosurgical generator when utilized as source 1.

In the illustrated arrangement, voltage setting resistor 66 and diode 60 generally set the voltage produced for cleaning and serve to rectify such voltage. Bypass resistor 68 is beneficial in that it reduces the total voltage that diode 60 needs to withstand when electrosurgical instrument 4 is not in electrical contact with cleaning assembly 64 or patient 5. In this regard, the bypass resistor 68 is selected such that its resistance is greater than that represented by cleaning assembly 64. By way of example, when the cleaning assembly 64 is designed to present a resistance of 200 ohms, bypass resistor 68 could have a resistance of about 500 ohms or more. Further, the resistance of bypass resistor 68 should be selected in conjunction with the breakdown voltage specifications of diode 60, the output voltage characteristics of the electrosurgical generator 1, and the resulting drop in voltage that would occur across the voltage setting resistor 66. Mechanical switch 70 is provided for selective actuation by a user when the user wishes to clean electrosurgical instrument 4. By way of example, mechanical switch 70 could be conveniently located as a separate button in the handle of electrosurgical instrument 4. One or more blocking capacitors 72 may be included to block biased electrical energy flows through the patient 5 in the event that a user actuates mechanical switch 70 and contacts the patient 5 with the electrosurgical instrument 4. In this case, the desired electrosurgical affect would occur in the usual way with a slight reduction in applied power due to the shunting of electrical energy through the voltage setting resistor 66, diode 60 and bypass resistor 68 via mechanical switch 70.

FIG. 6C illustrates an embodiment similar to that shown in FIG. 6B. In this embodiment, electrical energy is again utilized from electrosurgical generator 1 and applied via closed mechanical switch 70 for cleaning eschar from electrosurgical instrument 4. In this embodiment, capacitor 93 and diode 60 are employed to generally set the voltage produced for cleaning and for rectifying such voltage. A filter is defined by diode 63 and capacitor 92 so as to smooth the output voltage delivered to cleaning assembly 64. Use of voltage setting capacitor 11 (e.g. instead of a resistor) avoids the need to dissipate considerable heat. The filter (i.e. defined by diode 63 and capacitor 92) yields an output voltage to cleaning assembly 64 that consistently stays above zero volts, thereby facilitating the operation of cleaning assembly 64 when the electrosurgical instrument 4 is in electrical contact therewith. During surgical procedures, switch 70 is open and the return current path is through return electrode 6. Mechanical switch 70 is closed when a user wishes to clean the electrosurgical instrument 4. Again, mechanical switch 70 may be conveniently located in the handle of electrosurgical pencil or incorporated into the cleaning assembly 64.

As will be appreciated, the various electronic components and mechanical switch components shown in FIGS. 6B and 6C can be incorporated into electrosurgical generator 1, an assembly for return electrode 6, an assembly for electrosurgical instrument 4, or into combinations of the foregoing. For example, all of the electronic components shown in FIG. 6B, with the exception of blocking capacitor 72, could be readily incorporated into a connector for electrosurgical instrument 4 that plugs into electrosurgical generator 1. The blocking capacitor 72 could be readily incorporated into a connector for return electrode 6 that plugs into electrosurgical generator 1. Alternatively, all of these components could be included into one connector that would serve to connect both the electrosurgical instrument 4 and return electrode 6 into the electrosurgical generator 1.

Figure 6D:
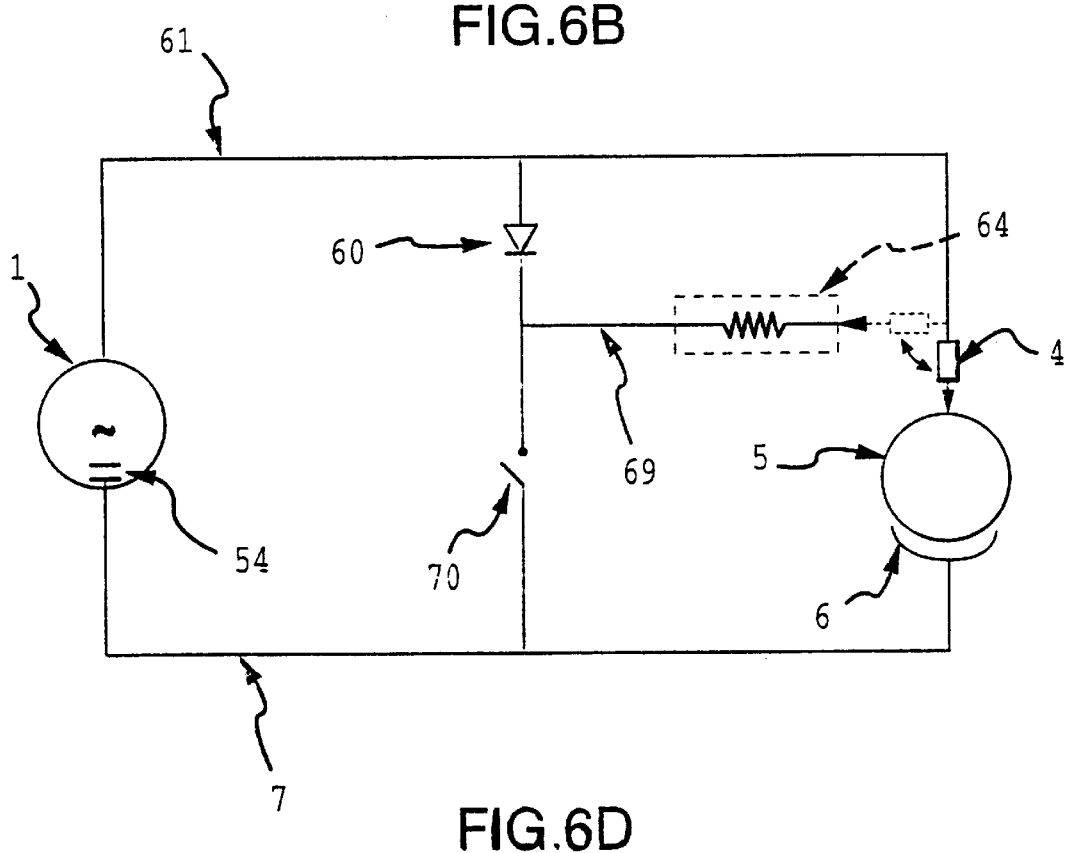

FIG. 6D illustrates another modified version of the arrangement of FIG. 6B. In FIG. 6B, the voltage difference across diode 60 is employed to provide a substantially positive voltage on the line 69 connected to cleaning assembly 64, relative to a substantially negative voltage on power line 61 to electrosurgical instrument 4. The unidirectional flow of current through the diode 60 causes the blocking capacitor 54 to become biased and produce a time-varying voltage waveform at cleaning assembly 64 that is positive relative to the voltage at the electrosurgical instrument 4.

To provide for selective cleaning and otherwise prevent a short-circuit from the return electrode line 7 to the supply line 61, an electronic, automatic switching element 70 may be employed. More particularly, such electronic switching element 70 may comprise one or more components such a bipolar junction transistor, an insulated gate bi-polar transistor, or a metal oxide semiconductor field effect transistor. When electrosurgical instrument 4 is not contacting the cleaning assembly 64, switch 70 effectively blocks all current flow through the line to diode 60. When the electrosurgical instrument 4 contacts cleaning assembly 64, current flows from the instrument 4 to the cleaning assembly 64 and switch 70 allows the current to flow.

Figure 6E:
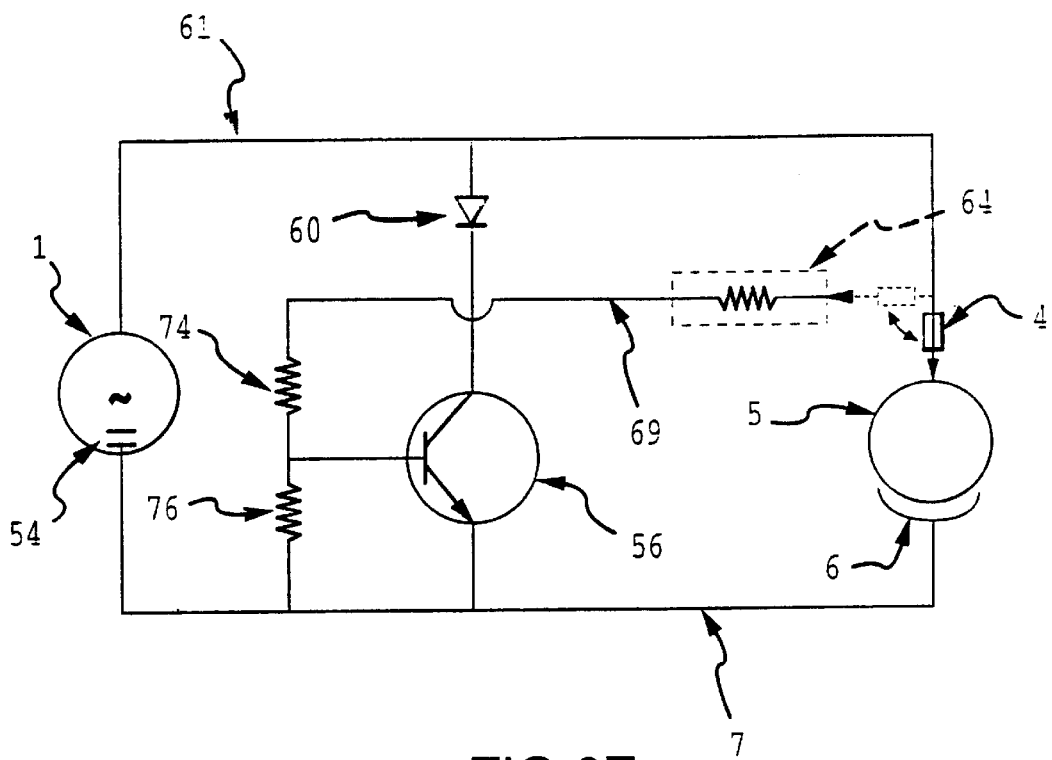

FIG. 6E shows yet another arrangement wherein a bi-polar junction transistor 56 and two resistors 74 and 76 can be provided to provide the switching function of switch 70 in FIG. 6B. Resistor 76 is selected to provide a relatively large resistance so that current flow during normal operation of generator 1 (i.e. when instrument 4 is not contacting cleaning assembly 64) through diode 60 is relatively low. During normal generator operation, the current flow through resistors 74 and 76, although low, causes cleaning power line 69 to become positively biased compared to the return line 7, and even more positively biased when compared to the supply line 61. Resistor 76 is further selected so that during normal operation of generator 1, the voltage difference between the base and emitter of transistor 56 does not exceed that which would cause transistor 56 to turn on. During cleaning, electrosurgical instrument 4 contacts cleaning assembly 64 and causes the voltage in cleaning line 69 to drop, changing the voltage difference between the base and emitter of transistor 56 to exceed the predetermined value necessary to turn the transistor on.

As will be appreciated, various circuit elements can be added to the arrangements of FIG. 6A–6E to control the current or voltage used for cleaning. As to FIG. 6E, such control elements may include any circuit component that will serve to moderate the magnitude of the control signal provided to the transistor 56, or an alternative transistor arrangement. Such transistor arrangement may be defined by one or more electronic components, at least one of which has its electrical conductivity across its input and output controlled by the voltage or current applied to one or more lines. By way of example, transistors appropriate for the present invention include one or more bi-polar transistors, insulated gate bi-polar transistors, or metal oxide semiconductor field effect transistors, although other devices could be employed including vacuum tubes or mechanical relay switches as noted above. As will be appreciated by those skilled in the art, when the transistor being employed is a bi-polar transistor, the control component should be a resistor that controls the current flow into the transistor's base.

Figure 6F:
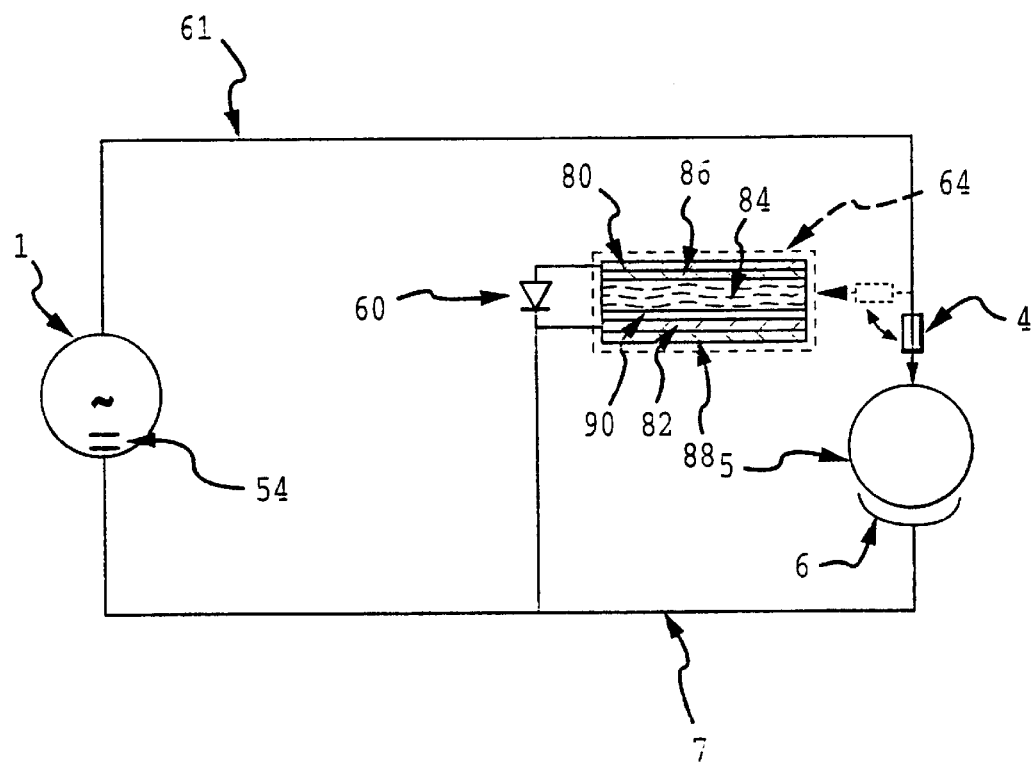

Instead of utilizing a mechanical or electronic switching element to control electrical power flow, as per the arrangements of FIGS. 6A–6E, a multiple element cleaning assembly 64 as shown in FIG. 6F may be employed. Such assembly 64 includes one or more electrically conductive elements that are either directly or indirectly connected to either the return electrode line 7, the supply line 4 or both of such lines. In this embodiment, the cleaning assembly 64 includes an upper conductor 80 and lower conductor 82 which are connected to opposing ends of diode 60. In this arrangement, the electrosurgical instrument 4 may be inserted into the cleaning assembly 64 (to establish electrical contact with upper conductor 80, thereby completing an electrical circuit across the diode 60). When the electrosurgical generator 1 is operating, the unidirectional passage of current through the diode 60 causes a substantially positive voltage to build up on the blocking capacitor 54. Such build-up in turn provides for a substantially positive voltage at the top conductor 80 relative to the voltage at the bottom conductor 82. The eschar on the electrosurgical instrument 4 is then submerged into an conductive liquid 84 which is contained within a housing defining cleaning assembly 64. Current flows between the bottom conductor 82 and the submerged portion of electrosurgical instrument 4 causing the eschar thereupon to be released. If a porous member (not shown) is provided to retain the electrolyte solution 84, such material may be utilized for engagement with the electrosurgical instrument 4 (e.g. in a wiping action) to facilitate removal of loosened eschar. Alternatively, an inside insulator member 86 may be utilized for such purposes. In this regard, the top conductor 80 in cleaning assembly 64 is kept from contacting the electrolyte solution 84 by the insulator member 86. Similarly, the conductive portion of the submerged electrosurgical instrument 4 is prevented from contacting the bottom conductor 82 by mechanical barrier 90. While mechanical barrier 90 prevents physical contact, it allows electrolytic current to pass therethrough. In this regard, for example, the mechanical barrier 90 could be a porous plastic screen with small openings that do not allow the submerged portion of the electrosurgical instrument 4 to pass therethrough, but which permits the electrically conductive (e.g., charge carrying) components of the conductive liquid solution to pass therethrough. The upper insulator 86 may be of similar construction (although not being submerged within the electrolyte solution 84). The bottom conductor 82 is insulated to the outside by the provision of bottom insulator 88, thereby facilitating safe handling of the housed cleaning assembly 64.

Figure 7:
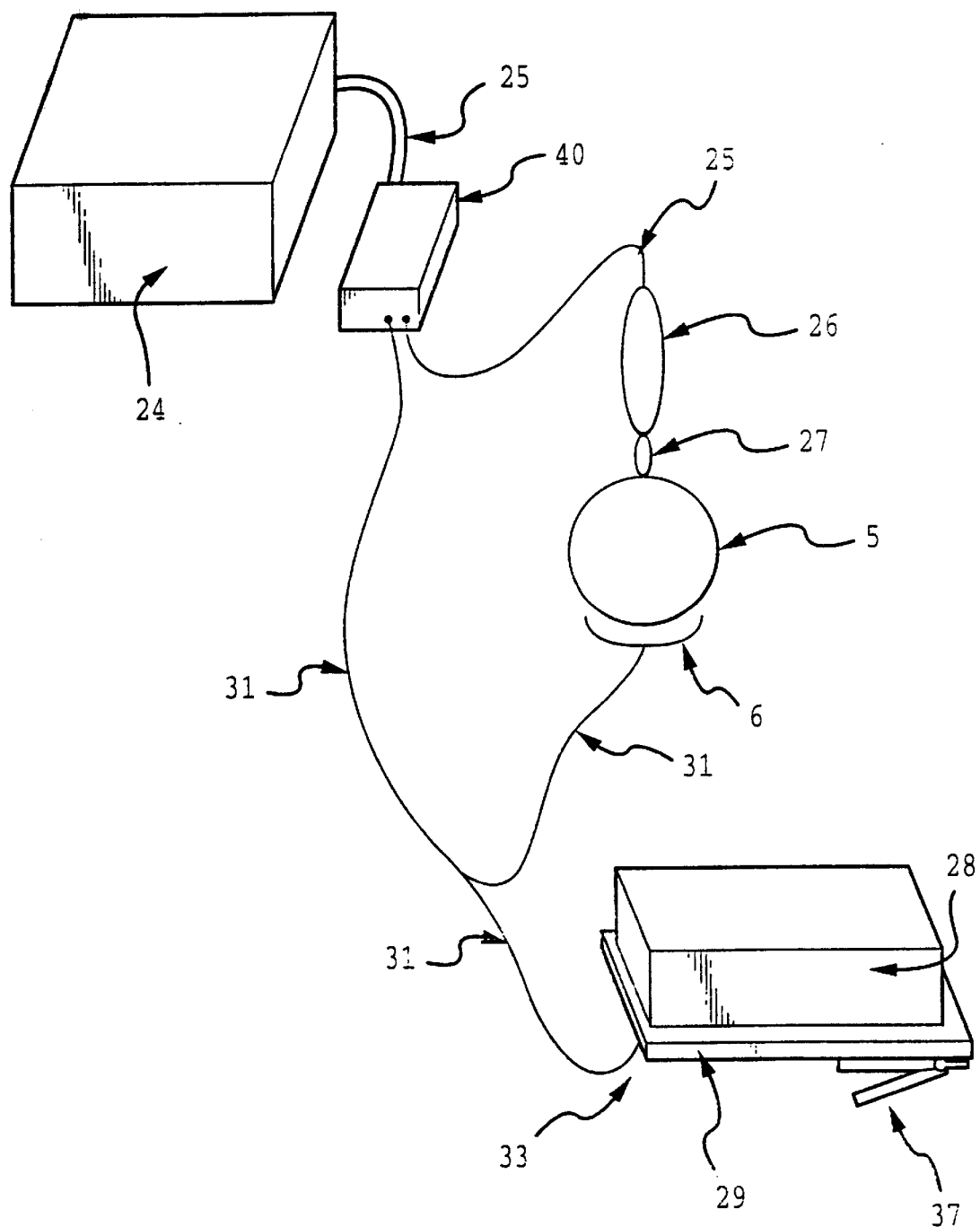
FIG. 7 illustrates how a monopolar electrosurgical system can be configured with a grounded cleaning pad to facilitate removing eschar from an electrosurgical instrument.

FIG. 7 illustrates an embodiment in which an RF electrical waveform generator 24 capable of producing RF waveforms suitable for use in electrosurgery is connected via electrically conductive insulated cable 25 to electrosurgical instrument 26. A waveform biasing device 40 may be included between RF source 24 and instrument 26 to provide an LF waveform and to combine the RF and LF waveforms, as described above in relation to FIGS. 5A–5E. Additionally, waveform biasing device 40 may provide for use of RF generator 24 for use in cleaning electrosurgical instrument 26 using a cleaning assembly 33, wherein circuitry components as per FIGS. 6A–6F are incorporated in device 40.

Attached to electrosurgical instrument 26 is metallic cutting element 27. When energized, the metallic cutting element 27 applies energy to the tissue of patient 5 and the electrical circuit is completed via return path electrode 6 and return path conductive wire 31. As noted, cleaning assembly 33 may be included to clean the metallic cutting element 27. For purposes of illustration, the cleaning assembly 33 comprises a cleaning pad 28, although other configurations are possible. Cleaning pad 28 may comprise a fibrous material which is wetted with a conductive, biocompatible solution (e.g., a normal saline solution and for solutions including ascorbic acid). For example, cleaning pad 28 may be made from woven or nonwoven absorbent materials (e.g., gauze). Cleaning pad 28 is attached to an electrically conductive backing 29 (e.g., a metal foil member). The faces and edges of the electrically conductive backing 29 which do not contact the cleaning pad 28 are preferably insulated with an electrically nonconductive material (not shown for clarity). The electrically conductive backing 29 is electrically connected via conductive element 30 to the return path conductive wire 31, and device 40 for operation as discussed in relation to FIGS. 6A–6F.

Metallic cutting element 27 includes working surfaces that contact or come in proximity to the tissue. Such surfaces are made from one or more electrically conductive materials and may be partly or completely covered with a nonmetallic coating that could impart desirable surface properties, such as stick resistance, although stick resistance is generally not needed with many aspects of the present invention for ease of eschar removal. Metallic cutting element 27 may be made from stainless steel, as is traditional for surgical instrument working surfaces.

Improved performance in the form of reduced or more easily removed eschar buildup occurs when cutting element 27 contains one or more materials that have standard reduction potentials that are positive with respect to that of a standard hydrogen electrode. Elements selected from group IB from the Periodic Chart of Elements are preferred, including copper, silver, and gold. The working surfaces of cutting element 27 may consist entirely of materials having standard reduction potentials positive with respect to that of the standard hydrogen electrode, or alloys that contain these materials combined. For example, excellent results occur with copper-based alloys comprising over 98 percent copper, brass that is approximately 70 percent copper and 30 percent zinc, or bronze that is approximately 95 percent copper, including phosphor bronze.

The cleaning pad 28 with its attached electrically conductive metal foil backing 29 and conductive element 30 may be packaged together in a product so as to maintain sterility during shipping and storage. These elements could be packaged separately or included as part of sterile package also containing the return path electrode 6 and return path conductive wire 31 assembly. Alternatively, the cleaning pad 28 with its attached electrically conductive metal foil backing 29 and conductive element 30 could be part of a package containing the electrically conductive insulated cable 25, electrosurgical instrument 26, and metallic cutting element 27. In one embodiment the cleaning pad 28 can be prewetted with the electrically conductive solution and packaged with its attached electrically conductive metal foil backing 29 in a sealed package that keeps the prewetted pad 28 from drying out. This sealed package could be included as a part of another package. In one embodiment the prewetting is done with normal saline, although other solutions, including ascorbic acid, are effective.

The assembly consisting of the cleaning pad 28 and its attached electrically conductive metal foil backing 29 may have other backing material attached. The additional backing in one embodiment would provide an electrically insulating surface on all of the exposed edges and back of the conductive foil backing 29. The additional backing in additional embodiments would make the assembly stiff to facilitate its use if a surgeon desires to press the working surfaces against the wetted pad 28 and wipe the working surfaces against the pad. Alternatively, this assembly may be left flexible so that a surgeon could pick it up and fold the pad 28 around the working surfaces to clean them. The assembly may also have a mechanism, such as a drape clip 37, attached to its back so that the assembly can be removably connected to drapes or other items convenient for health care personnel to use. Such mechanisms could include devices with one or a plurality of hooks, such as those on hook and loop fasteners.

Figure 8:
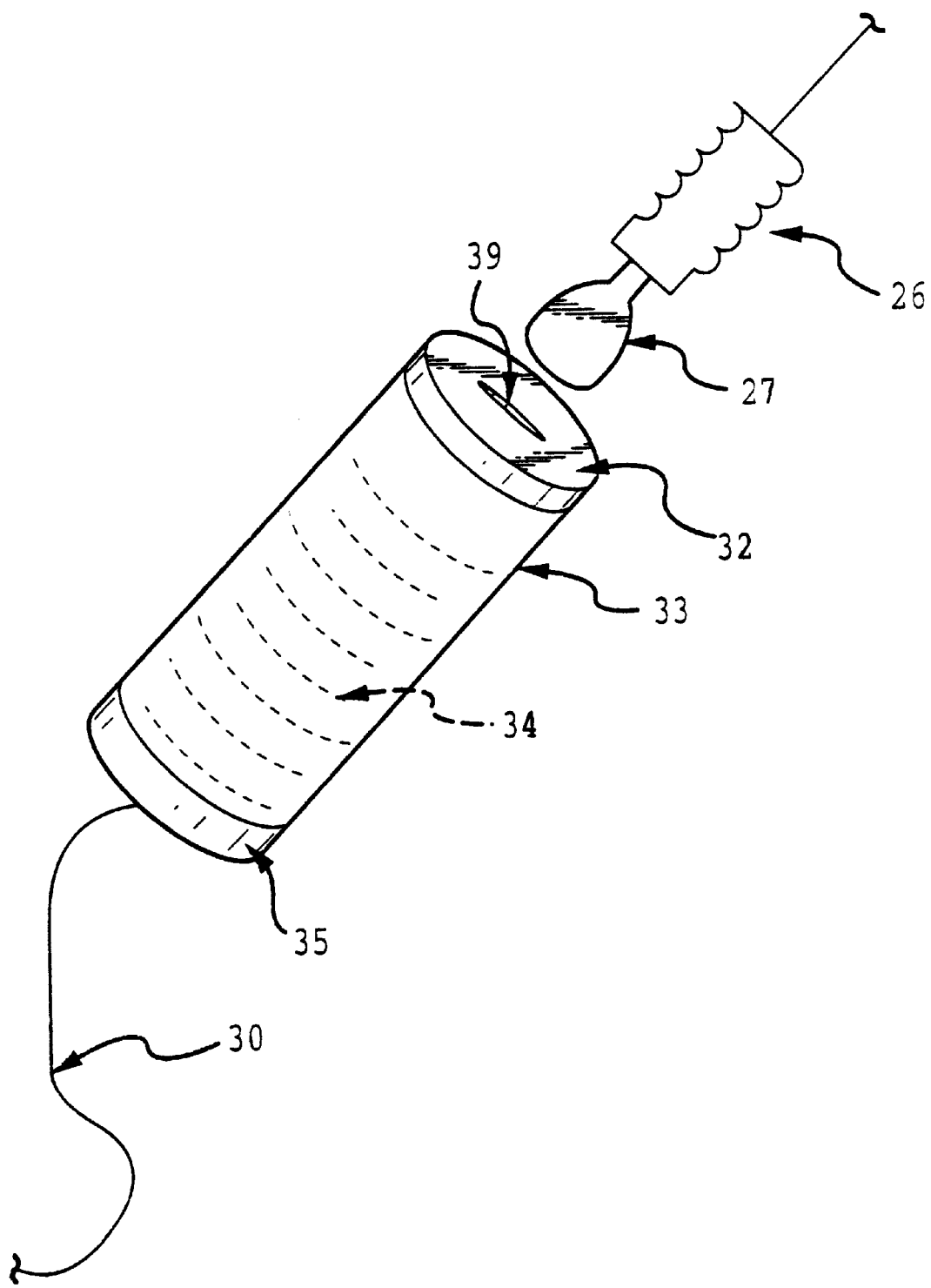
FIG. 8 illustrates an enclosed cleaning element into which working surfaces can be submerged in an electrically conductive liquid to facilitate removing eschar from an electrosurgical instrument.

FIG. 8 illustrates another embodiment of a cleaning assembly 33. Access cap 32 connects to a reservoir body 33, which contains conductive liquid 34 and is sealed at the bottom with bottom cap 35. Access cap 32 has a slot or other suitable opening 39 that allows metallic cutting element 27 to pass through and become submerged in conductive liquid 34. The conductive liquid 34 can be held in a structure (not shown), such as a sponge, that restricts it from flowing out through the opening 39 in the access cap 32. The material adjacent to opening 39 in access cap 32 is preferably selected to collapse around the metallic cutting element 27 as the metallic cutting element 27 is inserted/withdrawn, and otherwise serves to seal opening 39. By contacting the metallic cutting element 27, the edges of opening 39 in access cap 32 can facilitate removing eschar by wiping the metallic cutting element 27. Such features can be provided using a variety of means, including making access cap 32 from a flexible or elastomeric material that deforms when under force from the contact of the metallic cutting element 27 and returns to its sealed position when not under force.

In one embodiment the conductive liquid 34 is normal saline, although other solutions, including ascorbic acid, are effective. Conductive liquid 34 is either in direct electrical contact with conductive element 30, in which case conductive element 30 passes through bottom cap 35, or it is in indirect electrical contact with conductive element 30, in which case conductive element 30, is connected to the outside of bottom cap 35, which in turn would be electrically conductive with an outer insulating member positioned thereabout (not shown). The assembly may be shipped in a package (not shown) which maintains sterility during shipping and storage. These elements could be packaged as a separate assembly or included as part of sterile package also containing the return path electrode 6 and return path conductive wire 31 assembly shown in FIG. 7. Alternatively, the assembly could be part of the package containing the electrically conductive insulated cable 25, electrosurgical instrument 26, and metallic cutting element 27 shown in FIG. 7. The assembly may also have a mechanism, such as a drape clip, attached to its back so that the assembly can be removably connected to drapes or other items convenient for health care personnel to use. Such mechanisms could include devices with one or a plurality of hooks, such as those on hook and loop fasteners.

FIG. 8 illustrates having the bottom cap 35 being connected to the conductive element 30 such that the electrical return path is external to the cleaning assembly 33. In another embodiment, the access cap 32 can be conductive, such as by having a conductive foil layer (not shown), that is in turn connected to one terminal of a substantially DC current source (not shown). The other terminal of the substantially DC current source is connected to conductive element 30. When metallic cutting element 27 passes through access cap 32 it takes on the polarity of the access cap 32 and when the metallic cutting element 27 contacts the conductive liquid 34 the electrical circuit that facilitates eschar removal is completed. The conductive liquid 34 can be held in a structure (not shown), such as a sponge, that keeps it from flowing out through the opening in the access cap 32.

Figure 9:
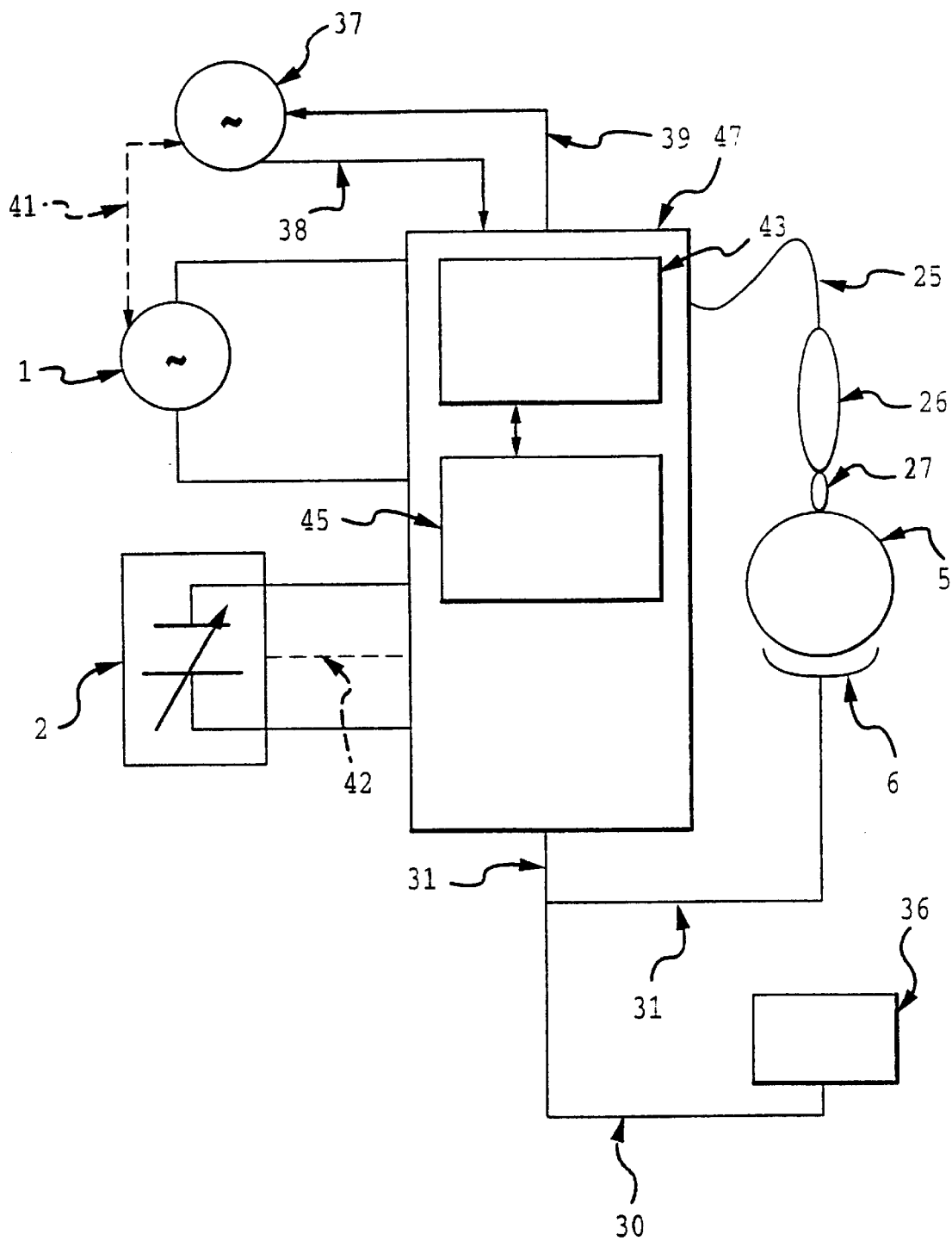
FIG. 9 illustrates an embodiment having RF and LF sources for enhanced electrosurgery and cleaning procedures, and which includes sensing control means for use in alternating between such procedures.

FIG. 9 schematically illustrates the inclusion of controls in one embodiment to sense when contact occurs between the working surfaces of an electrosurgical instrument 26, such as the metallic cutting element 27, and the electrically conductive solution in a blade cleaning apparatus 36 (e.g., such as the cleaning pad 28 of the FIG. 7 embodiment). Such controls could be implemented by, for example, sensing when a low impedance path exists between the metallic cutting element 27 and the blade cleaning apparatus 36. Such sensing could occur, for example, by using a support generator 37 to produce a sense signal (e.g., a 100–200 kHz AC or other time varying signal) that goes through a sense signal output conductor 38 and that has a ground return with sense circuit ground conductor 39. Both the sense signal output conductor 38 and the sense circuit ground conductor 39 connect to a circuit module 47 comprising a control logic device 43 and, a subcircuit 45 for combining the output of RF source 1 and LF source 2 (e.g. as per FIGS. 5A–E). The control logic device 43 in circuit module 47 will control when the RF source 1 and the LF source 2 operate and would, for example, have both of them operate concurrently during surgical procedures so as to combine their outputs for negative biasing utilizing signal combining subcircuit 45. The sense signal is selected so that it will work correctly in the use environment. For example, it could have a frequency in the range of 100 to 200 kilohertz and be limited to a current that does not exceed 5 milliamperes. The sense signal is sent to the metallic cutting element 27 via the electrically conductive insulated cable 25 and the electrosurgical instrument 26 and the returning signal's strength is sensed from the return path formed by the blade cleaning apparatus 36, the conductive element 30, and the return path conductive wire 31. The sense signal generator 37 produces the sense signal except when the RF source 1 is operating. When the RF source 1 is operating, the output from the sense signal generator 37 is stopped with a sense signal generator lockout signal 41.

When the metallic cutting element 27 contacts the conductive solution in the blade cleaning apparatus 36 a low impedance return path for the sense signal is created. When the metallic cutting element 27 is not contacting the conductive solution the sense signal circuit is open, thus presenting a very high impedance return path for the sense signal. The controls in the circuit 45 to combine RF and LF sources and the sense signal and control logic device 43 detect the low impedance path and activate the LF source 2 using an LF source voltage level control signal 42 to produce an electrical waveform with a higher range negative bias voltage of between approximately negative 30 and negative 120 volts. The RF source 1 would not be activated. The automatic activation of LF source 2 at the higher range would apply the electrical waveform to instrument 26 needed for eschar removal using apparatus 36. One embodiment would prevent the LF source 2 from producing a high negative bias voltage except when the working surfaces, such as the metallic cutting element 27, contact the electrically conductive solution in cleaning apparatus 31. This control prevents medical practitioners from inadvertently applying higher negative voltage bias electrical waveforms to patient tissues.

Control logic device 43, for example, sense when the working surfaces 27 contact the cleaning apparatus 38 by detecting the presence of the sense signal in conductive return path 31 using a detector circuit that employs suitable combinations of high pass and low pass filters to attenuate signals with frequencies above and below those of the sense signal. The amplitude of the filtered signal could be used, possibly in combination with suitable amplifiers, as an input to a threshold detector to determine whether the detected sense signal is strong enough to establish that the working surfaces are contacting the cleaning apparatus. The threshold detectors could include, for example, voltage comparators that use a reference voltage as a threshold that is compared to an amplified filtered sense signal. If the sense signal is strong enough then the threshold detector would produce an output signal that drives a switching circuit that directs cleaning power to the electrosurgical instrument. Similarly, if the filtered signal's strength is below that required for the threshold detector to produce an output signal that drives a switching circuit for cleaning the control logic circuit then the control logic circuit enables switching circuits that lead to normal electrosurgical device operation, which could include operating RF source 1 and LF source 2, as described above. The circuitry that generates the sense signal could be used to simultaneously produce the comparison signal so that not only the proper amplitude but also the proper timing of the sense signal is used to establish whether the working surfaces are contacting the cleaning apparatus. Detecting both amplitude and timing can improve the reliability of the automatic sensing logic. Such an approach can be particularly effective when the sense signal is generated in a manner that is other than a continuous wave, such as if it has times when the signal is present and times when the signal is absent and a comparison circuit checks for the presence and absence of the sense signal occurring at the correct times.

A spray element that produces a mist of a conductive biocompatible substance can be incorporated into the surgical instrument 26, as taught by U.S. Pat. No. 5,554,172, hereby incorporated by reference in its entirety, or the mist can be generated and applied using a separate device. Employing such a mist while applying electrical energy during surgical procedures is known to those skilled in the art. However, use of such a spray or mist with a negative average bias waveform for electrosurgery is novel. Such an inventive arrangement yields further enhanced results.

OPERATION

The use of the present invention will be described in the context of the embodiment of the embodiment of FIG. 9 for monopolar cutting. It can be readily seen that the invention could be used with other types of surgical procedures. As such, the invention is not limited to the application described.

In use, the health care professional would follow standard practice and prepare the surgical site in the usual way. The electrical waveform generator's 1 provides a plurality of power settings for proper selection depending upon the procedure to be performed. A standard setup would be applying the return path electrode 6 from the patient to the electrical waveform generator 1 is established via the return path conductive wire 31. Also included in the standard setup is the connection of electrosurgical instrument 26 to the electrical waveform generator 1 via electrically conductive insulated cable 25. Where cleaning apparatus 36 includes an assembly as shown in FIG. 7, cleaning pad 28 with its attached electrically conductive metal foil backer 29 and conductive element 30 are removed from a package (not shown) which maintains sterility during shipping and storage. The conductive element 30 is connected so that electrical continuity exists to the electrical return path 31 of the electrical waveform generator 1. If the cleaning pad 28 is not yet wetted, then it is wetted with normal saline. The cleaning pad 28 with its attached electrically conductive metal foil backer 29 and any other backer and attachment device that may be part of the assembly are put in a location convenient for the surgeon. Clipping to a drape near the surgical site would be likely.

Cutting and other surgical procedures occur in a conventional fashion. When eschar is to be removed from the working surfaces of hand held instrument 26, such as the metallic cutting element 27, they are gently pressed against the cleaning pad 28. The module 47 may be provided to sense the contact between the working surfaces and the cleaning pad 28 and automatically activates the LF source 2 to produce the correct electrical waveform. The energy for this electrical waveform flows from the source 2 through the electrically conductive insulated cable 25, through the electrosurgical instrument 26, through the metallic cutting element 27, and into the cleaning pad 28 (which is wet with normal saline) and its attached electrically conductive metal foil backer 29. Almost immediately (e.g., within 1 to 10 seconds), whatever eschar is present loosens and either falls off the working surfaces or is easily wiped from the working surfaces with no apparent effort. With little delay, and with the now clean working surfaces, the surgeon can continue with the surgical procedure.

In the case where conductive solution is sprayed on the working surfaces, cutting and other surgical procedures occur in the usual way and as the spray mist is directed at the working surfaces. Little, if any, eschar forms and adheres to the working surfaces when the working surfaces are made from a, for example, copper-based substance.

The above-described embodiments are for purposes of illustration only. Numerous modifications and extensions will be apparent those skilled in the art and are intended to be within the scope of the present invention as contemplated by the claims that follow.

What is claimed is:

1. An electrosurgical apparatus for providing an electrosurgical signal to an electrosurgical instrument in an electrosurgical circuit comprising an electrosurgical instrument and an electrosurgical return path device, the electrosurgical apparatus comprising:

means for providing a negative-biasing signal component; and means for combining said negative-biasing signal component with a radio frequency signal component to provide an electrosurgical signal, wherein said means for combining is interconnectable with an electrosurgical instrument to define a negative mean voltage bias at the electrosurgical instrument relative to an electrosurgical return path device.

2. An apparatus as recited in claim 1 further comprising:
an electrosurgical generator for providing said radio frequency signal component.

3. An apparatus as recited in claim 2, said means for providing including:
an electrical energy source separate from said electrosurgical generator.

4. An apparatus as recited in claim 3, wherein said electrical energy source comprises at least one of a direct current energy source and a time-varying energy source.

5. An apparatus as recited in claim 4, wherein said radio frequency signal component has a minimum first frequency and said negative biasing signal component has a maximum second frequency, said first frequency being greater than said second frequency, and wherein said apparatus further comprises:
at least one of a first frequency-biased blocking component and a first frequency-based shunting component to isolate said time-varying energy source from said radio frequency signal component; and
at least one of a second frequency-based blocking component and a second frequency based shunting component to isolate said electrosurgical generator from said negative-biasing signal component.

6. An apparatus as claimed in claim 2, wherein said means for providing utilizes said radio-frequency signal component to generate said negative biasing signal component.

7. An apparatus as claimed in claim 1, further comprising:
a hand-held electrosurgical instrument defining said supply path and having working surfaces comprising stainless steel.

8. An apparatus as claimed in claim 1, further comprising:
a hand-held electrosurgical instrument defining said supply path and having working surfaces comprising at least one material from the group comprising: copper, silver and gold.

9. An apparatus as claimed in claim 1, further comprising:
a hand-held electrosurgical instrument defining said supply path; and
means for applying an electrical signal, separate from said electrosurgical signal, to said electrosurgical instrument during a cleaning procedure.

10. An apparatus as claimed in claim 9, further comprising:
a cleaning assembly for receiving said electrosurgical instrument during said cleaning procedure, comprising:
a conductive liquid; and
a return electrode in electrical contact with said liquid.

11. An apparatus for cleaning eschar from a surgical instrument comprising:
means for physically receiving a surgical instrument during a non-surgical cleaning procedure, including:
means for containing an electrically conductive medium for electrical contact with a surgical instrument during a non-surgical cleaning procedure; and
an electrically conductive return electrode for electrically contacting a conductive medium contained by said means for containing; and means for separately applying an electrical cleaning signal to said surgical instrument during a non-surgical cleaning procedure.

12. An apparatus as claimed in claim 11, wherein said means for applying is operable to maintain said instrument at a negative electrical potential relative to said return electrode.

13. An apparatus as claimed in claim 11, wherein said conductive medium comprises a conductive fluid, and said apparatus further comprises:
a housing means for retaining said conductive fluid.

14. An apparatus as claimed in claim 11, further comprising:
means for automatically activating said means for applying upon contact between said instrument and said conductive medium.

15. An apparatus as claimed in claim 11, further comprising:
an electrosurgical generator for providing a source signal; and
means for using said source signal to provide said electrical cleaning signal.

16. An electrosurgical method for obtaining at least one predetermined surgical effect at a tissue site, comprising:
supplying an electrosurgical signal to a working surface of an electrosurgical instrument;
providing an electrical signal return path from said tissue site; and
conveying electrical energy to the tissue site from said working surface, wherein the working surface has a negative average voltage bias relative to the return path.

17. An electrosurgical method as recited in claim 16, said supplying step including:
combining a first signal component and a second signal component to obtain said electrosurgical signal.

18. An electrosurgical method as recited in claim 17, said supplying step further including:
utilizing a radio frequency electrosurgical generator to generate said first signal component.

19. An electrosurgical method as recited in claim 18, said supplying step further including:
employing said first signal component to obtain said second signal component.

20. An electrosurgical method as recited in claim 19, wherein said first signal component has a first frequency and said second signal component has a second frequency, said second frequency being less than said first frequency.

21. An electrosurgical method as recited in claim 20, wherein said first frequency is more than about 100 kHz and said second frequency is less than about 10 kHz.

22. An electrosurgical method as recited in claim 18, said supplying step further including:
employing an electrical energy source, separate from said radio frequency electrosurgical generator, to provide said second signal component.

23. An electrosurgical method as recited in claim 22, further comprising:
utilizing at least one first frequency-biased blocking component to isolate said electrosurgical generator from said electrical energy source;
employing at least one second-frequency biased blocking component to isolate said electrical energy source from said electrosurgical generator.

24. An electrosurgical method as recited in claim 22, wherein said electrical energy source is selected from the group comprising:

a DC energy source, and a time-varying energy source having an operating frequency less than an operating frequency of the radio frequency electrosurgical generator.

25. An electrosurgical method as recited in claim 19, wherein said second signal component is a DC signal.

26. An electrosurgical method as recited in claim 17, further comprising:

cleaning said working surface of said electrosurgical instrument, wherein said cleaning step includes:
applying an electrical cleaning signal, different from said electrosurgical signal, to said working surface.

27. An electrosurgical method as recited in claim 26, further comprising:

contacting said electrosurgical instrument with a conductive liquid;

contacting a conductive return electrode with said conductive liquid, wherein a negative voltage bias is provided at said electrosurgical instrument relative to said return electrode.

28. The method of claim 16, wherein the average bias voltage exceeds about 1 volt.

29. The method of claim 28, wherein the average bias voltage is between about 1 and 60 volts.

30. The method of claim 16, wherein the working surface comprises stainless steel.

31. The method of claim 16, wherein the working surface comprises at least one material having a standard reduction potential that is positive with respect to a standard hydrogen electrode.

32. The method of claim 31, wherein the working surface comprises at least one material selected from a group comprising the elements of Group IB of the Periodic Chart of Elements.

33. The method of claim 32, wherein the working surface comprises at least one of the group comprising, copper, silver and gold.

34. The method of claim 16, further comprising:

spraying the working surfaces with a conductive liquid during at least said conveying step.

35. A method for cleaning eschar from a surgical instrument during a nonsurgical cleaning procedure comprising:

separately applying an electrical cleaning signal to a surgical instrument during a non-surgical cleaning procedure; and contacting said surgical instrument with a medium for cleaning the surgical instrument during at least a portion of said applying step to remove eschar from the surgical instrument.

36. A method as claimed in claim 35, wherein said medium is electrically conductive, and further comprising:

contacting a conductive return electrode with said conductive medium during said portion of said applying step, wherein a negative voltage bias is provided at said instrument relative to said return electrode.

37. The method of claim 36, wherein said medium is a conductive liquid, and the contacting step comprises:

submerging working surfaces of the instrument in the conductive liquid.

38. The method of claim 37, wherein the conductive liquid is retained in a container.

39. The method of claim 38, wherein the container comprises contact means for selectively establishing electrical contact between the instrument and the conductive liquid upon insertion of the instrument into said container.

40. The method of claim 38, wherein the container includes attachment means for selectively, supportably attaching the container to a support surface.

41. The method of claim 36, wherein said medium comprises a conductive liquid retained by an absorbent member, and further comprising:

wiping the surfaces against said absorbent member.

42. The method of claim 36, wherein the negative voltage bias is greater than about 10 volts.

43. The method of claim 42, wherein the negative voltage bias is between about 10 and about 120 volts.

44. The method of claim 35, wherein the electrical signal is defined by a substantially direct current.

45. The method of claim 44, wherein the direct current has a bias voltage greater than about 10 volts.

46. A method as claimed in claim 35, further comprising:

utilizing an electrosurgical generator to provide said electrical signal.

47. A method as claimed in claim 46, said utilizing step including:

rectifying an RF output of said electrosurgical generator.

48. A method as claimed in claim 47, wherein said rectifying step includes:

utilizing at least one diode.

* * * * *